US012723050B2

United States Patent
(12) United States Patent
Liu et al.

(10) Patent No.: US 12,723,050 B2
(45) Date of Patent: Sep. 1, 2026

(54) CRYSTAL FORM OF COMPOUND AND USE THEREOF

(71) Applicant: TENNOR THERAPEUTICS (SUZHOU) LIMITED, Suzhou (CN)

(72) Inventors: Yu Liu, Suzhou (CN); Wenhui Yao, Suzhou (CN); Zeqin Wu, Suzhou (CN); Zhenkun Ma, Suzhou (CN)

(73) Assignee: TENNOR THERAPEUTICS (SUZHOU) LIMITED, Suzhou (CN)

(*) Notice: Subject to any disclaimer, the term of this patent is extended or adjusted under 35 U.S.C. 154(b) by 0 days.

(21) Appl. No.: 19/434,116

(22) Filed: Dec. 29, 2025

(65) Prior Publication Data

US 2026/0132148 A1 May 14, 2026

Related U.S. Application Data

(63) Continuation of application No. PCT/CN2024/102004, filed on Jun. 27, 2024.

(30) Foreign Application Priority Data

Jul. 10, 2023 (CN) ......................... 202310841754.9

(51) Int. Cl.
*C07D 498/22* (2006.01)
*A61K 31/438* (2006.01)
*A61K 45/06* (2006.01)

(52) U.S. Cl.
CPC .......... *C07D 498/22* (2013.01); *A61K 31/438* (2013.01); *A61K 45/06* (2013.01)

(58) Field of Classification Search
CPC .................................................... C07D 498/22
See application file for complete search history.

(56) References Cited

U.S. PATENT DOCUMENTS 5,095,108 A 3/1992 Konstantinova et al.

FOREIGN PATENT DOCUMENTS

CN 104628745 A 5/2015
CN 104710439 A 6/2015
CN 105037389 A 11/2015
CN 108047250 A 5/2018
WO 2008/008480 A2 1/2008

OTHER PUBLICATIONS

International Search Report issued Sep. 18, 2024, in International Application No. PCT/CN2024/102004 (with attached English Translation).

Zhenkun MA et al., "Design, Synthesis, and Characterization of TNP-2198, a Dual-Targeted Rifamycin-Nitroimidazole Conjugate with Potent Activity Against Microaerophilic and Anaerobic Bacterial Pathogens," J. Med. Chem., vol. 65, (2022) pp. 4481-4495.

*Primary Examiner* — John S Kenyon

(74) *Attorney, Agent, or Firm* — Merchant & Gould P.C.; Daniel J. Pereira

(57) ABSTRACT

The present application provides crystal forms A and B of a free base of a compound represented by formula (I), and relates to a use of the crystal forms A and B Formula (I)

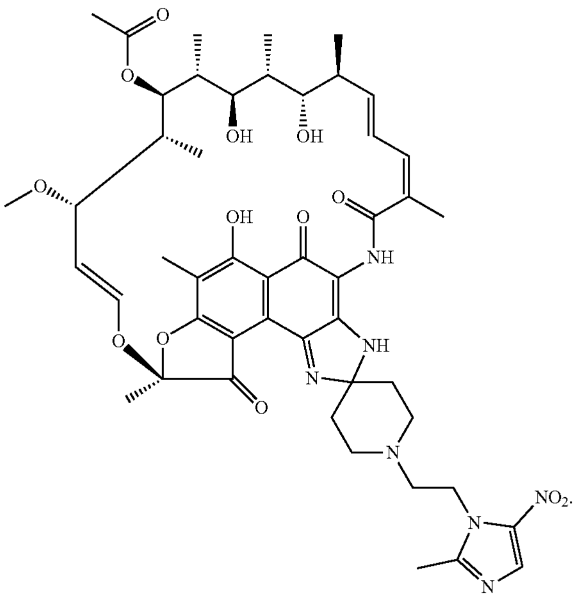

10 Claims, 18 Drawing Sheets

CRYSTAL FORM OF COMPOUND AND USE THEREOF

CROSS-REFERENCE TO RELATED APPLICATION

The present application is a Continuation of PCT International Application No.: PCT/CN2024/102004 filed on Jun. 27, 2024, which claims priority to Chinese Patent Application 202310841754.9, filed Jul. 10, 2023, the disclosure of which is incorporated herein by reference in its entirety.

TECHNICAL FIELD

The present application relates to the field of biomedicine, and in particular to the crystal forms of a compound and uses thereof.

BACKGROUND

Rifamycins are natural products with potential antimicrobial activity. Rifamycins of natural sources (e.g., rifamycin B, rifamycin O, rifamycin R, rifamycin U, rifamycin S, rifamycin SV, and rifamycin Y (Brufani, M., Cerrini, S., Fedeli, W., Vaciago, A. *J. Mol. Biol.* 1974, 87, 409-435)) has limited therapeutic applications due to, for example, poor pharmacokinetics, low oral bioavailability, weak activity against gram-negative pathogens, and low distribution in infected tissues. In the prior art, various semisynthetic rifamycin derivatives with improved antibacterial spectrum and pharmacological properties have been produced through chemical modifications. Among such semisynthetic compounds, rifampicin and rifabutin, for example, have been developed as therapeutics currently used for the treatment of tuberculosis and other microbial infections (Farr, B. F. Rifamycins, in Principles and Practice of Infectious Diseases; Mandell, G. L., Bennett, J. E., Dolin, R., Eds.; Churchill Livingstone Philadelphia; pp. 348-361). TNP-2198 is a dual-targeting rifamycin-nitroimidazole conjugate that has potent activity against microaerophilic and anaerobic bacterial pathogens and exhibits good activity against strains resistant to both rifamycins and nitroimidazoles. However, the development and application of such innovative drug molecules with antibacterial activity are often affected by such physicochemical properties as high relative molecular mass, high lipophilicity, low water solubility, hygroscopicity, and the like as well as bioavailability and stability (chemical stability, thermal stability, melting point, crystal form stability) of the free forms, making it difficult to meet the requirements for formulation druggability. Therefore, the search and screening for new molecular entities (e.g., salt forms or crystal forms) of such parent drug molecules are crucial to their pharmaceutical applications.

SUMMARY

The present application provides a crystal form of free base of a compound satisfying multiple pharmaceutical requirements to overcome the defects in the prior art.

In one aspect, the present application provides crystal form A of free base of compound represented by formula (I), formula (I)

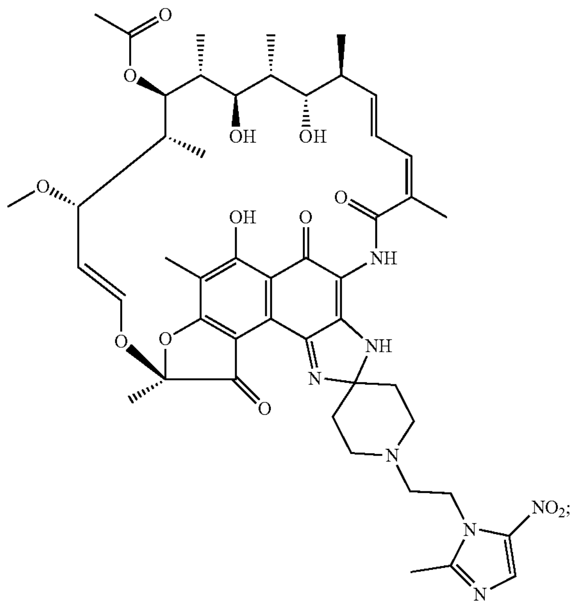

;

wherein the crystal form A exhibits an X-ray powder diffraction pattern having characteristic peaks at diffraction angles 2θ of 5.28°±0.2°, 7.17°±0.2°, 8.50°±0.2°, 10.66°±0.2°, 14.33°±0.2°, 15.84°±0.2°, and 18.60°±0.2°.

In some embodiments, the crystal form A has characteristic peaks at one or more of diffraction angles 2θ of 12.61°±0.2°, 14.83°±0.2°, 15.26°±0.2°, 16.57°±0.2°, 19.97°±0.2°, and 21.97°±0.2°.

In some embodiments, the crystal form A has characteristic peaks at diffraction angles 2θ of 12.61°±0.2°, 14.83°±0.2°, 15.26°±0.2°, 16.57°±0.2°, 19.97°±0.2°, and 21.97°±0.2°.

In some embodiments, the crystal form A exhibits an X-ray powder diffraction (XRPD) pattern substantially consistent with FIG. 1.

In some embodiments, the differential scanning calorimetry curve of the crystal form A has an endothermic peak at about 169.3° C.

In some embodiments, the differential scanning calorimetry (DSC) plot of the crystal form A is substantially consistent with FIG. 2B.

In some embodiments, the crystal form A is an anhydrate and/or a non-solvate.

In another aspect, the present application provides crystal form B of the free base of the compound represented by formula (I), wherein the crystal form B exhibits an X-ray powder diffraction pattern having characteristic peaks at diffraction angles 2θ of 4.89°±0.2°, 6.67°±0.2°, 7.12°±0.2°, 13.41°±0.2°, 14.62°±0.2°, 15.19°±0.2°, and 18.23°±0.2°.

In some embodiments, the crystal form B exhibits an X-ray powder diffraction pattern having characteristic peaks at one or more of diffraction angles 2θ of 7.84°±0.2°, 10.67°±0.2°, 14.25°±0.2°, 16.07°±0.2°, 17.10°±0.2°, 17.41°±0.2°, 17.74°±0.2°, and 20.73°±0.2°.

In some embodiments, the crystal form B exhibits an X-ray powder diffraction pattern having characteristic peaks at diffraction angles 2θ of 7.84°±0.2°, 10.67°±0.2°, 14.25°±0.2°, 16.07°±0.2°, 17.10°±0.2°, 17.41°±0.2°, 17.74°±0.2°, and 20.73°±0.2°.

In some embodiments, the crystal form B exhibits an X-ray powder diffraction (XRPD) pattern substantially consistent with FIG. 3.

In some embodiments, the differential scanning calorimetry curve of the crystal form B has endothermic peaks at about 85.6° C., about 130.7° C., and about 144.3° C.

In some embodiments, the differential scanning calorimetry (DSC) plot of the crystal form B is substantially consistent with FIG. 4B.

In some embodiments, the crystal form B is obtained by converting the crystal form A described in the present application in a toluene reagent.

In some embodiments, the crystal form B is a toluene solvate.

In some embodiments, a molar ratio of the compound represented by formula (I) to toluene molecules in the crystal form B is 1:2 to 1:1.

In another aspect, the present application provides crystal form B of the free base of the compound represented by formula (I), wherein the differential scanning calorimetry curve of the crystal form B has endothermic peaks at about 85.6° C., about 130.7° C., and about 144.3° C.

In some embodiments, the differential scanning calorimetry (DSC) plot of the crystal form B is substantially consistent with FIG. 4B.

In some embodiments, the crystal form B is obtained by converting the crystal form A described in the present application in a toluene reagent.

In some embodiments, the crystal form B is a toluene solvate.

In some embodiments, a molar ratio of the compound represented by formula (I) to toluene molecules in the crystal form Bis 1:2 to 1:1.

In another aspect, the present application provides a pharmaceutical composition, wherein the pharmaceutical composition comprises the crystal form A described in the present application and/or the crystal form B described in the present application, and optionally a pharmaceutically acceptable carrier.

In some embodiments, the pharmaceutical composition further comprises a second therapeutic agent. In some embodiments, the second therapeutic agent is selected from: a proton pump inhibitor, an acid suppressant, an efflux pump inhibitor, an anesthetic, an antifungal agent, an antiviral agent, an antibacterial agent, an antiprotozoal agent, an anti-inflammatory agent, an anticoagulant, a platelet aggregation inhibitor, an antipyretic, a lipid-lowering agent, and a zinc salt.

In another aspect, the present application provides a kit, wherein the kit comprises one or more of the crystal form A described in the present application, the crystal form B described in the present application, and the pharmaceutical composition described in the present application.

In some embodiments, the kit further comprises written instructions for use and/or machine-readable electronic instructions for use.

In another aspect, the present application provides a method for preparing a medicament using the crystal form A described in the present application and/or the crystal form B described in the present application.

In another aspect, the present application provides a method for inhibiting or preventing bacterial growth, wherein the method comprises administering an effective amount of one or more of the crystal form A described in the present application, the crystal form B described in the present application, the pharmaceutical composition described in the present application, and the kit described in the present application.

In another aspect, the present application provides a method for preventing, treating, or ameliorating a disease or related disorders thereof, wherein the method comprises administering to a patient in need an effective amount of one or more of the crystal form A described in the present application, the crystal form B described in the present application, the pharmaceutical composition described in the present application, and the kit described in the present application.

In some embodiments, the patient in need is infected with bacteria.

In some embodiments, the bacteria are selected from: *Helicobacter pylori, Mycobacterium tuberculosis, Nontuberculous mycobacteria, Acinetobacter baumannii, Bacteroides fragilis, Bifidobacterium longum, Ruminococcus, Prevotella, Clostridium perfringens, Clostridium difficile, Lactobacillus acidophilus, Eggerthella lenta, Fusobacterium nucleatum, Gardnerella vaginalis, Mobiluncus mulieris, Peptostreptococcus, Porphyromonas asaccharolytica, Prevotella bivia, Propionibacterium acnes*, and *Veillonella parvula.*

In another aspect, the present application provides use of the crystal form A described in the present application, the crystal form B described in the present application, the pharmaceutical composition described in the present application, and/or the kit described in the present application in inhibiting or preventing bacterial growth.

In another aspect, the present application provides use of the crystal form A described in the present application, the crystal form B described in the present application, the pharmaceutical composition described in the present application, and/or the kit described in the present application in preparing a medicament for preventing, treating, or ameliorating a disease caused by bacterial infections or related disorders thereof.

In some embodiments, the bacteria are selected from: *Helicobacter pylori, Mycobacterium tuberculosis, Nontuberculous mycobacteria, Acinetobacter baumannii, Bacteroides fragilis, Bifidobacterium longum, Ruminococcus, Prevotella, Clostridium perfringens, Clostridium difficile, Lactobacillus acidophilus, Eggerthella lenta, Fusobacterium nucleatum, Gardnerella vaginalis, Mobiluncus mulieris, Peptostreptococcus, Porphyromonas asaccharolytica, Prevotella bivia, Propionibacterium acnes*, and *Veillonella parvula.*

In some embodiments, the disease or the related disorders thereof are selected from: gastritis, gastric ulcer, bacterial vaginosis, diarrhea, pneumonia, appendicitis, cholecystitis, otitis media, endocarditis, endometritis, brain abscess, myocardial necrosis, osteomyelitis, peritonitis, empyema, salpingitis, septic arthritis, liver abscess, sinusitis, pelvic inflammatory disease, and bacteremia; and upper respiratory tract infections, lower respiratory tract infections, skin and soft tissue infections, bone and joint infections, lung infections, intra-abdominal infections, eye infections, ear infections, oral infections, and surgical infections.

In another aspect, the present application provides the pharmaceutical composition described in the present application or the kit described in the present application for use in preventing, treating, or ameliorating a disease caused by bacterial infections or related disorders thereof.

In some embodiments, the bacteria are selected from: *Helicobacter pylori, Mycobacterium tuberculosis, Nontuberculous mycobacteria, Acinetobacter baumannii, Bacte-*

*roides fragilis, Bifidobacterium longum, Ruminococcus, Prevotella, Clostridium perfringens, Clostridium difficile, Lactobacillus acidophilus, Eggerthella lenta, Fusobacterium nucleatum, Gardnerella vaginalis, Mobiluncus mulieris, Peptostreptococcus, Porphyromonas asaccharolytica, Prevotella bivia, Propionibacterium acnes*, and *Veillonella parvula.*

In some embodiments, the disease or the related disorders thereof are selected from: gastritis, gastric ulcer, bacterial vaginosis, diarrhea, pneumonia, appendicitis, cholecystitis, otitis media, endocarditis, endometritis, brain abscess, myocardial necrosis, osteomyelitis, peritonitis, empyema, salpingitis, septic arthritis, liver abscess, sinusitis, pelvic inflammatory disease, and bacteremia; and upper respiratory tract infections, lower respiratory tract infections, skin and soft tissue infections, bone and joint infections, lung infections, intra-abdominal infections, eye infections, ear infections, oral infections, and surgical infections.

In another aspect, the present application provides a method for preparing the crystal form A described in the present application, wherein the method comprises crystallizing the compound represented by formula (I) in a solvent comprising an alcohol solvent, wherein the alcohol solvent is selected from one of or a combination of more than one of methanol, ethanol, n-propanol, isopropanol, n-butanol, isobutanol, and tert-butanol.

Furthermore, the method of preparing the crystal form A described in the present application further comprises crystallizing the compound represented by formula (I) in an alcohol solvent.

In some embodiments, the alcohol solvent is methanol, ethanol, or a combination thereof.

In some embodiments, the method further comprises concentrating the alcohol solvent to obtain a concentrated wet product, and drying the concentrated wet product.

In another aspect, the present application provides crystal form A of the free base of the compound represented by formula (I), wherein the crystal form A is obtained by the method for preparing the crystal form A described in the present application.

In another aspect, the present application provides a method for preparing the crystal form B described in the present application, wherein the method comprises crystallizing the crystal form A described in the present application in a toluene solvent.

In another aspect, the present application provides crystal form B of the free base of the compound represented by formula (I), wherein the crystal form B is obtained by the method for preparing the crystal form B described in the present application.

Other aspects and advantages of the present application will be readily apparent to those skilled in the art from the following detailed description. Only exemplary embodiments of the present application have been shown and described in the following detailed description. As those skilled in the art will recognize, the content of the present application enables those skilled in the art to make changes in the specific embodiments disclosed without departing from the spirit and scope of the invention to which the present application relates. Accordingly, the description in the drawings and specification of the present application is provided only for the purpose of illustration rather than limitation.

BRIEF DESCRIPTION OF THE DRAWINGS

The specific features of the invention to which the present application relates are set forth in the appended claims. The features and advantages of the invention to which the present application relates may be more fully understood with reference to the exemplary embodiments and drawings described in detail below. The drawings are briefly described below:

DETAILED DESCRIPTION

Figure 1:
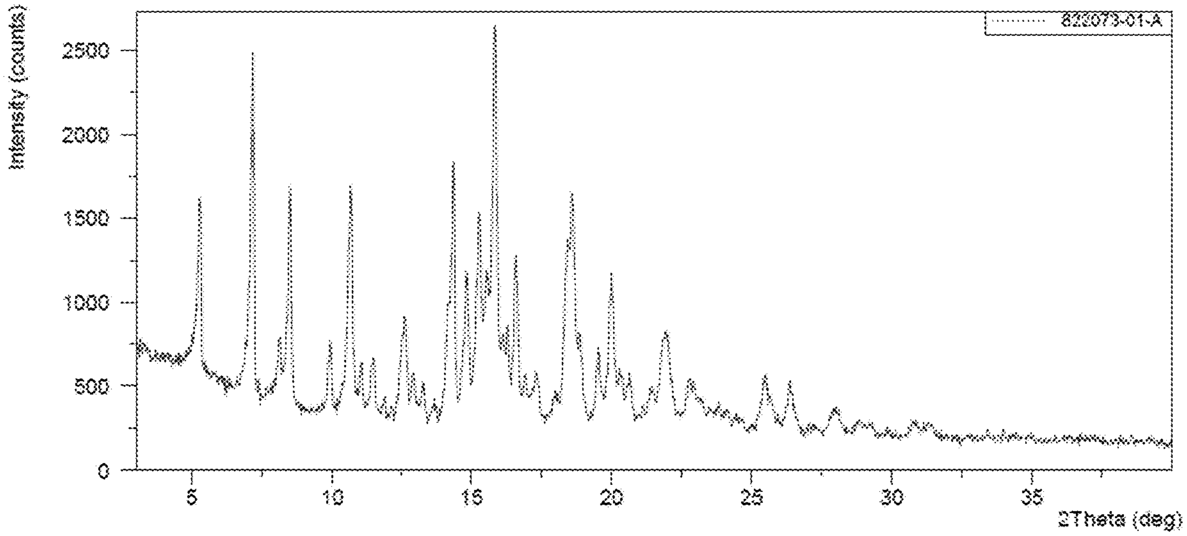
FIG. 1 shows the XRPD pattern of the crystal form A of the present application.

The implementation of the invention of the present application is described below with reference to specific embodiments, and those skilled in the art can easily understand other advantages and effects of the invention of the present application from the disclosure of this specification.

Definitions of Terms

In the present application, the term "substantially consistent with (a figure) . . . " generally means that information such as the number of characteristic peaks, the position (or distribution) of characteristic peaks, and the geometric topological rules in the patterns is largely the same or similar. For example, the characteristic peaks involved in the present application may be the diffraction peaks in an X-ray powder diffraction (XRPD) pattern, the endothermic peaks in a differential scanning calorimetry (DSC) plot, the chemical shift peaks in a hydrogen nuclear magnetic resonance ($^1$H NMR) spectrum, the absorption peaks in a high-performance liquid chromatography (HPLC) chromatogram, or the like. For example, the term "substantially consistent with (a figure) . . . " can mean that at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the characteristic peaks in the pattern are shown in the reference figure.

In the present application, the term "2θ (also known as 2theta or diffraction peak) value" pertaining to X-ray powder diffraction (XRPD) patterns is expressed in degrees) (°. When referring to patterns and/or data therein, the term "diffraction peak" generally refers to a feature that one skilled in the art would not attribute to background noise. For the X-ray powder diffraction peaks of the crystal forms described in the present application, the measured values of the 2θ or the diffraction peaks in the X-ray powder diffraction patterns may have experimental errors, which may occur between one instrument and another, as well as between one sample and another, potentially resulting in slight differences in the measured values of the 2θ or the diffraction peaks in the X-ray powder diffraction patterns. The numerical values of the experimental errors or the differences may be about ±0.2 units, ±0.1 units, or ±0.05 units. Therefore, the numerical values of the 2θ or the diffraction peaks cannot be considered absolute.

In certain embodiments, the differential scanning calorimetry (DSC) plot of the crystal forms may also have experimental errors, which may occur between one instrument and another, as well as between one sample and another, potentially resulting in slight differences in the positions and the peak values of the endothermic peaks. The numerical values of the experimental errors or the differences may be less than or equal to 5° C., less than or equal to 4° C., less than or equal to 3° C., less than or equal to 2° C., or less than or equal to 1° C. Therefore, the numerical values of the peak positions or the peak values of the DSC endothermic peaks cannot be considered absolute.

In certain embodiments, the thermogravimetric analysis (TGA) of the crystal forms may also have experimental errors, which may occur between one instrument and another, as well as between one sample and another, potentially resulting in slight differences in the weight loss temperature and the amount of weight loss. The numerical values of the experimental errors or the differences may be approximately ±0.1 units, approximately ±0.05 units, or approximately ±0.01 units. Therefore, the numerical values of the weight loss temperature and the amount of weight loss cannot be considered absolute.

In the present application, all numbers disclosed herein are approximate values, whether or not the word "approximately" or "about" is used, and the numerical value of each number may vary, for example, by ±1%, ±2%, ±5%, or the like. The term "about" or "approximately" is generally within an acceptable error range as determined by those of ordinary skills in the art for a particular value, which may depend in part on how the value is measured or determined, i.e., the limitations of the measurement system. For example, "about" or "approximately" may mean being within 1 or more than 1 standard deviation as per the practice in the art. Alternatively, "about" or "approximately" may mean a range of up to 10% or 20% (i.e., ±10% or ±20%). For example, about 3 mg may include any number between 2.7 mg and 3.3 mg (for 10%) or between 2.4 mg and 3.6 mg (for 20%). Furthermore, particularly with respect to biological systems or processes, the term may mean a value of up to an order of magnitude or a value of up to 5-fold. Unless otherwise specified, when a particular value or composition is provided in the specification and the appended claims, the meaning of "about" or "approximately" should be assumed to be within an acceptable error range for the particular value or composition.

In the present application, the term "solvate" and "solvate adduct/complex" are used interchangeably and generally refer to an association compound or complex of one or more solvent molecules with the compound described in the present application. Examples of solvents for forming solvates include, but are not limited to, water, isopropanol, ethanol, methanol, DMSO, ethyl acetate, acetic acid, and ethanolamine.

In the present application, the term "pharmaceutically acceptable carrier" generally refers to one or more non-toxic materials that do not interfere with the effectiveness of the biological activity of the active ingredient. Such formulations may routinely contain a salt, a buffering agent, a preservative, a compatible carrier, and optionally an additional therapeutic agent. Such pharmaceutically acceptable formulations may also comprise a compatible solid or liquid filler, a diluent, or an encapsulating substance suitable for administration to a human. Other contemplated carriers, excipients, and/or additives that can be used in the formulations described herein may include, for example, flavoring agents, antimicrobial agents, sweeteners, antioxidants, antistatic agents, lipids, protein excipients (e.g., serum albumin, gelatin, and casein), salt-forming counterions (e.g., sodium), etc. These and other known pharmaceutical carriers, excipients, and/or additives suitable for use in the formulations described herein are known in the art, for example, as listed in "Remington: The Science & Practice of Pharmacy", 21st ed., Lippincott Williams & Wilkins (2005), and "Physician's Desk Reference", 60th ed., Medical Economics, Montvale, New Jersey (2005). The suitable pharmaceutically acceptable carrier may be routinely determined based on the desired or required mode of administration, solubility, and/or stability.

In the present application, the term "therapeutic agent" generally refers to a compound (including but not limited to a pharmaceutically acceptable salt, a hydrate, a solvate, a crystal form, a prodrug, a metabolite, a deuteride, or the like thereof), a mixture of compounds, a composition, a biological macromolecule, or an extract made from biological materials capable of inducing a desired therapeutic effect, preventing the development of a certain disorder, or alleviating the related disorder when properly administered to a patient.

In the present application, the term "bacteria" generally refers to a class of prokaryotic organisms without distinct nuclei and membranous organelles. The bacterium may include spherical, rod-shaped, or spiral species. The bacteria may include species that grow interlink, for example, *Escherichia, Salmonella, Shigella, Klebsiella, Vibrio, Pasteurella, Borrelia, Leptospira, Campylobacter, Clostridium, Corynebacterium, Yersinia, Treponema, Rickettsia, Chlamydia, Mycoplasma, Coxiella, Neisseria, Listeria, Haemophilus, Helicobacter, Legionella, Pseudomonas, Bordetella, Brucella, Staphylococcus, Streptococcus, Enterococcus, Bacillus, Mycobacterium, Nocardia*, etc. The term "bacterial infection" generally refers to any disorder caused by the expansion and/or presence of bacteria described in the present application in a cell or a subject. The bacterial infections can be caused by the growth and reproduction of bacteria (e.g., a pathogenic bacterium) that produces toxins and other metabolic products.

In the present application, the term "patient in need" may generally include human patients and other mammalian subjects receiving prophylactic or therapeutic treatment, including but not limited to non-human primates, laboratory animals such as rabbits, canines, rats, and mice, as well as other animals. The "patient in need" may illustratively be a subject diagnosed with a specific disease, a subject receiving treatment related to a specific disease, a subject with a tendency or risk of developing a specific disease, etc.

In the present application, the term "administer", "administration", or "administering" generally refers to introducing the drug or a composition comprising the drug (e.g., the therapeutic agent provided in the present application) into the body of a patient by any route of introduction or delivery. Any method known to those skilled in the art for bringing a cell, an organ, or a tissue into contact with the drug or the composition thereof can be employed.

In the present application, the term "effective amount" generally refers to an amount sufficient to achieve, or at least partially achieve, the desired therapeutic effect. The "effective amount" of a drug or therapeutic agent generally refers to an amount sufficient to cure, or at least partially arrest, a disease and its complications in a patient already suffering from the disease. The effective amount for this use will depend on the severity of the infection and the overall state of the patient's own immune system.

In the present application, the term "comprise" or "comprising" generally refers to the inclusion of the explicitly specified features without excluding other elements. The terms "not less than" and "not more than" generally refer to situations where the number itself is included.

In the present application, the term "selected from" generally refers to the inclusion of the selected objects and all combinations thereof. For example, "selected from(:) A, B, and C" refers to the inclusion of all combinations of A, B, and C, e.g., A, B, C, A+B, A+C, B+C, or A+B+C.

DETAILED DESCRIPTION OF THE INVENTION

In one aspect, the present application provides crystal form A of the free base of the compound represented by formula (I), wherein the crystal form A exhibits an X-ray powder diffraction pattern having characteristic peaks at diffraction angles 2θ of 5.28°±0.2°, 7.17°±0.2°, 8.50°±0.2°, 10.66°±0.2°, 14.33°±0.2°, 15.84°±0.2°, and 18.60°±0.2°.

In another aspect, the present application provides crystal form A of the free base of the compound represented by formula (I), wherein the differential scanning calorimetry curve of the crystal form A has an endothermic peak at about 169.3° C.

In another aspect, the present application provides crystal form B of the free base of the compound represented by formula (I), wherein the crystal form B exhibits an X-ray powder diffraction pattern having characteristic peaks at diffraction angles 2θ of 4.89°±0.2°, 6.67°±0.2°, 7.12°±0.2°, 13.41°±0.2°, 14.62°±0.2°, 15.19°±0.2°, and 18.23°±0.2°.

In another aspect, the present application provides crystal form B of the free base of the compound represented by formula (I), wherein the differential scanning calorimetry curve of the crystal form B has endothermic peaks at about 85.6° C., about 130.7° C., and about 144.3° C.

In another aspect, the present application provides a pharmaceutical composition, wherein the pharmaceutical composition comprises the crystal form A described in the present application and/or the crystal form B described in the present application, and optionally a pharmaceutically acceptable carrier.

In another aspect, the present application provides a kit, and the kit comprises one or more of the crystal form A described in the present application, the crystal form B described in the present application, and the pharmaceutical composition described in the present application.

In another aspect, the present application provides a method for preparing a medicament using the crystal form A described in the present application and/or the crystal form B described in the present application.

In another aspect, the present application provides a method for inhibiting or preventing bacterial growth, wherein the method comprises administering an effective amount of one or more of the crystal form A described in the present application, the crystal form B described in the present application, the pharmaceutical composition described in the present application, and the kit described in the present application.

In another aspect, the present application provides a method for preventing, treating, or ameliorating a disease or related disorders thereof, wherein the method comprises administering to a patient in need an effective amount of one or more of the crystal form A described in the present application, the crystal form B described in the present application, the pharmaceutical composition described in the present application, and the kit described in the present application.

In another aspect, the present application provides use of the crystal form A described in the present application, the crystal form B described in the present application, the pharmaceutical composition described in the present application, and/or the kit described in the present application in inhibiting or preventing bacterial growth.

In another aspect, the present application provides use of the crystal form A described in the present application, the crystal form B described in the present application, the pharmaceutical composition described in the present application, and/or the kit described in the present application in preparing a medicament for preventing, treating, or ameliorating a disease caused by bacterial infections or related disorders thereof.

In another aspect, the present application provides the pharmaceutical composition described in the present application or the kit described in the present application for use in preventing, treating, or ameliorating a disease caused by bacterial infections or related disorders thereof.

Crystal Forms of Free Base of Compound of Formula (I)

The present application provides crystal form A and crystal form B, and in certain cases, crystal form C1, crystal form C2, and crystal form C3. The following examples will help further understand these crystal forms, preparation methods therefor, use thereof, technical effects thereof, and the like described in the present application, but these examples are not intended to limit the content of the invention of the present application.

Pharmaceutical Composition

In some embodiments, the pharmaceutical composition described in the present application may be prepared in an optional formulation form. For example, the pharmaceutical composition may be in the form of a solution, an aerosol, a gel, an ointment, a spray, or a suspension. The compositions in the forms described above may be prepared using methods known and conventional in the art. For example, the pharmaceutically acceptable carrier may be selected from an excipient for increasing the solubility, an auxiliary agent for enhancing the viscosity, and an auxiliary agent for enhancing the osmotic capacity.

In some embodiments, the pharmaceutical composition may further comprise a second therapeutic agent. For example, the second therapeutic agent may be selected from an additional rifamycin drug or an analog thereof, a proton pump inhibitor, an acid suppressant, an efflux pump inhibitor, an anesthetic, an antifungal agent, an antiviral agent, an antibacterial agent, an antiprotozoal agent, an anti-inflammatory agent (e.g., a non-steroidal anti-inflammatory drug or a steroid), an anticoagulant, a platelet aggregation inhibitor, an antipyretic, a lipid-lowering agent, and a zinc salt. All therapeutic agents used in the pharmaceutical compositions described in the present application can be used in the dose range currently known and used for these formulations.

Kit

In some embodiments, the kit described in the present application may comprise the crystal form described in the present application and/or the pharmaceutical composition described in the present application; in addition, the kit may further comprise at least one container for placing the crystal form and/or a container for placing the pharmaceutical composition. For example, the kit may further comprise one or more components, and may further comprise a second, third, and/or additional containers other than the container, in which the one or more components may be separately placed. For example, the kit may further comprise various combinations of the crystal form and/or the pharmaceutical composition in the container(s). For example, the kit may further comprise a buffering reagent, a device for mixing different components, a device for measurement, a device for sorting components, and/or a device for labeling. For example, the kit may further comprise a package for receiving the various containers. For example, the kit may further comprise instructions for using the components of the kit. For example, the instructions may include a written paper form and/or a machine-readable electronic form.

Methods of Administration

In some embodiments, the method for inhibiting or preventing bacterial growth provided in the present application may comprise administering an effective amount of the crystal form described in the present application, the pharmaceutical composition described in the present application, and/or the kit described in the present application by an optional route. In some embodiments, the method comprises contacting the crystal form described in the present application, the pharmaceutical composition described in the present application, and/or the kit described in the present application with a site infected with bacteria. For example, the infected site may be an inner site or a surface site of an animal body, or an inner site or a surface site of a plant body.

In some embodiments, the method for preventing, treating, or ameliorating a disease or related disorders thereof provided in the present application may comprise administering to a patient in need an effective amount of the crystal form described in the present application, the pharmaceutical composition described in the present application and/or the kit described in the present application by an optional route. In certain embodiments, the method may further comprise mixing the crystal form described in the present application, the pharmaceutical composition described in the present application, and/or the kit described in the present application with an additional therapeutic agent. In some embodiments, the method may comprise systemically delivering the crystal form described in the present application, the pharmaceutical composition described in the present application, and/or the kit described in the present application in a patient in need, so as to expose the majority of the body to the treatment. The procedure may be performed by any means known in the art, including but not limited to intravenous, intra-arterial, subcutaneous, and intraperitoneal delivery. In other embodiments, the method may comprise locally delivering the crystal form described in the present application, the pharmaceutical composition described in the present application, and/or the kit described in the present application in a patient in need, so as to directly deliver the treatment to a target site in an organism or to a site infected by bacteria on the surface of an organism, or directly contact the treatment with a site infected with bacteria on the surface of an organism. For example, such local delivery does not exclude a systemic pharmacological effect. In certain embodiments, the method may comprise administering to a patient in need an effective amount of the crystal form described in the present application, the pharmaceutical composition described in the present application, and/or the kit described in the present application by intramuscular injection, subcutaneous or intradermal injection, intravenous injection, intrathecal injection, inhalation, oral administration, application on the body surface, etc.

Diseases Caused by Bacteria and Bacterial Infections or Related Disorders Thereof In some embodiments, the patient in need described in the present application is infected with bacteria, or the patient in need suffers from a disease caused by bacterial infections or related disorders thereof. For example, the bacteria may be selected from: *Helicobacter pylori, Mycobacterium tuberculosis, Nontuberculous mycobacteria, Acinetobacter baumannii, Bacteroides fragilis, Bifidobacterium longum, Ruminococcus, Prevotella, Clostridium perfringens, Clostridium difficile, Lactobacillus acidophilus, Eggerthella lenta, Fusobacterium nucleatum, Gardnerella vaginalis, Mobiluncus mulieris, Peptostreptococcus, Porphyromonas asaccharolytica, Prevotella bivia, Propionibacterium acnes*, and *Veillonella parvula*. In the present application, the bacteria may further comprise a drug-resistant strain of the bacteria described above. For example, the drug-resistant strain may be resistant to rifamycin, resistant to nitroimidazole, or resistant to both rifamycin and nitroimidazole. For example, the drug-resistant strain may also be resistant to other antibiotics, including macrolides, such as clarithromycin, azithromycin, and roxithromycin; fluoroquinolones, such as ciprofloxacin, levofloxacin, and moxifloxacin; aminoglycosides, such as streptomycin and amikacin; β-lactams, such as ampicillin and amoxicillin; tetracyclines, such as tetracycline, tigecycline, and minocycline; oxazolidinones, such as linezolid and tedizolid; nitrofurans, such as furazolidone; glycopeptides, such as vancomycin; diarylquinolines, such as bedaquiline; and clofazimine.

For example, the disease may be selected from gastritis, gastric ulcer, bacterial vaginosis, diarrhea, pneumonia, appendicitis, cholecystitis, otitis media, endocarditis, endometritis, brain abscess, myocardial necrosis, osteomyelitis, peritonitis, empyema, salpingitis, septic arthritis, liver abscess, sinusitis, pelvic inflammatory disease, and bacteremia. For example, the disorders may be selected from upper respiratory tract infections, lower respiratory tract infections, skin and soft tissue infections, bone and joint infections, lung infections, intra-abdominal infections, eye infections, ear infections, oral infections, and surgical infections.

Without being bound by any theory, the following examples are intended only to illustrate the crystal forms of the compound, the methods for preparing the same, use, etc. of the present application, but not to limit the scope of the invention of the present application.

EXAMPLES

Example 1

Figure 2A:
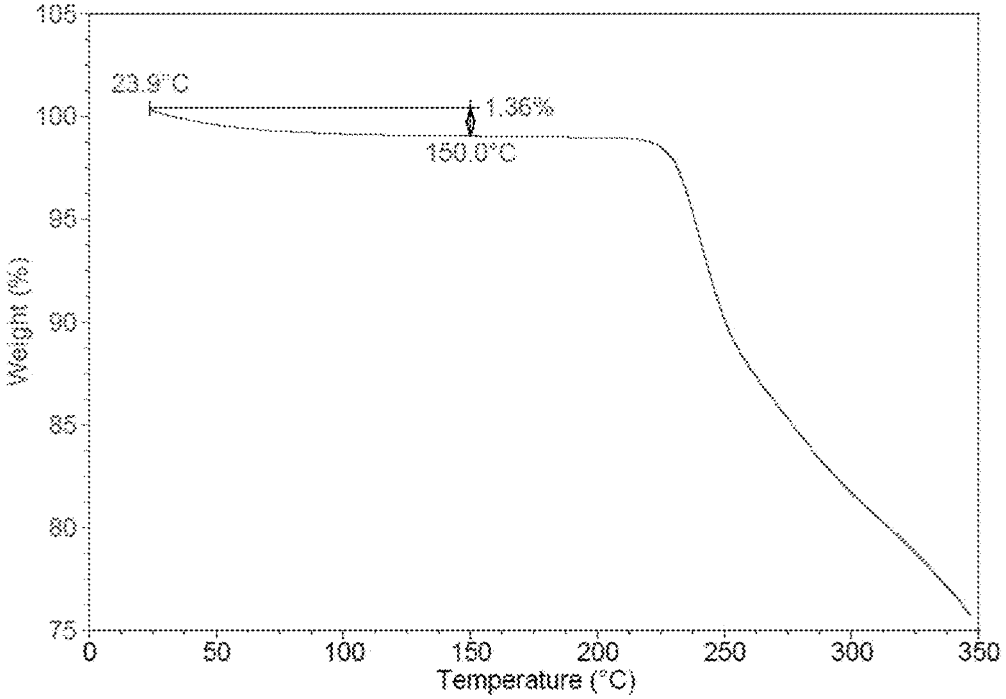
FIGS. 2A-2B show the TGA plot and the DSC plot of the crystal form A of the present application.
Figure 2B:
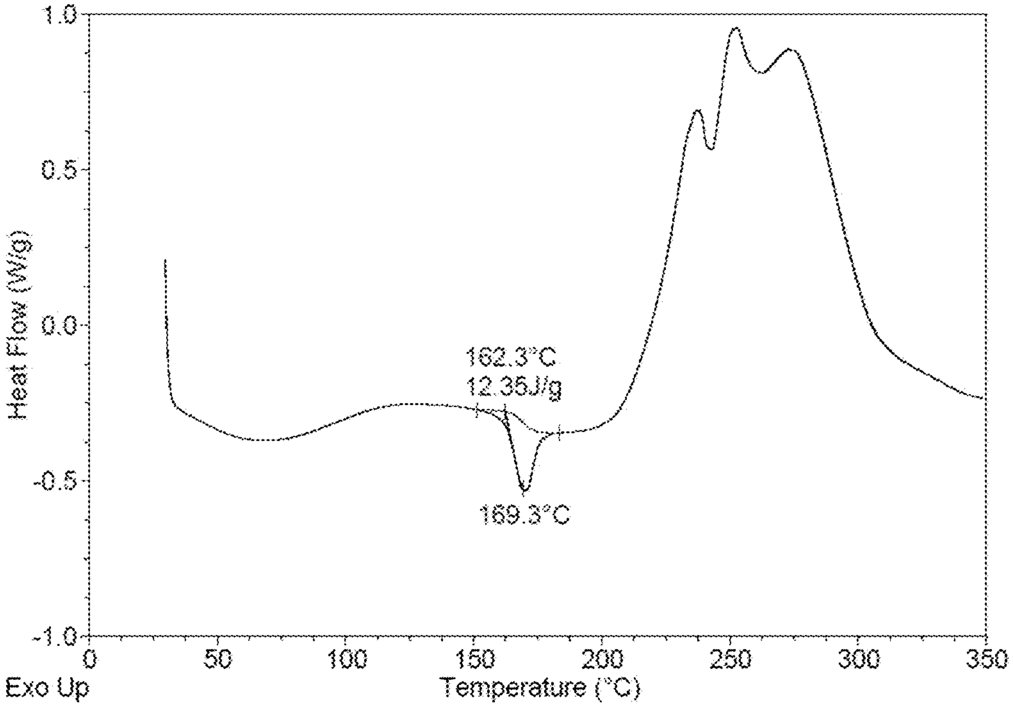
Figure 5:
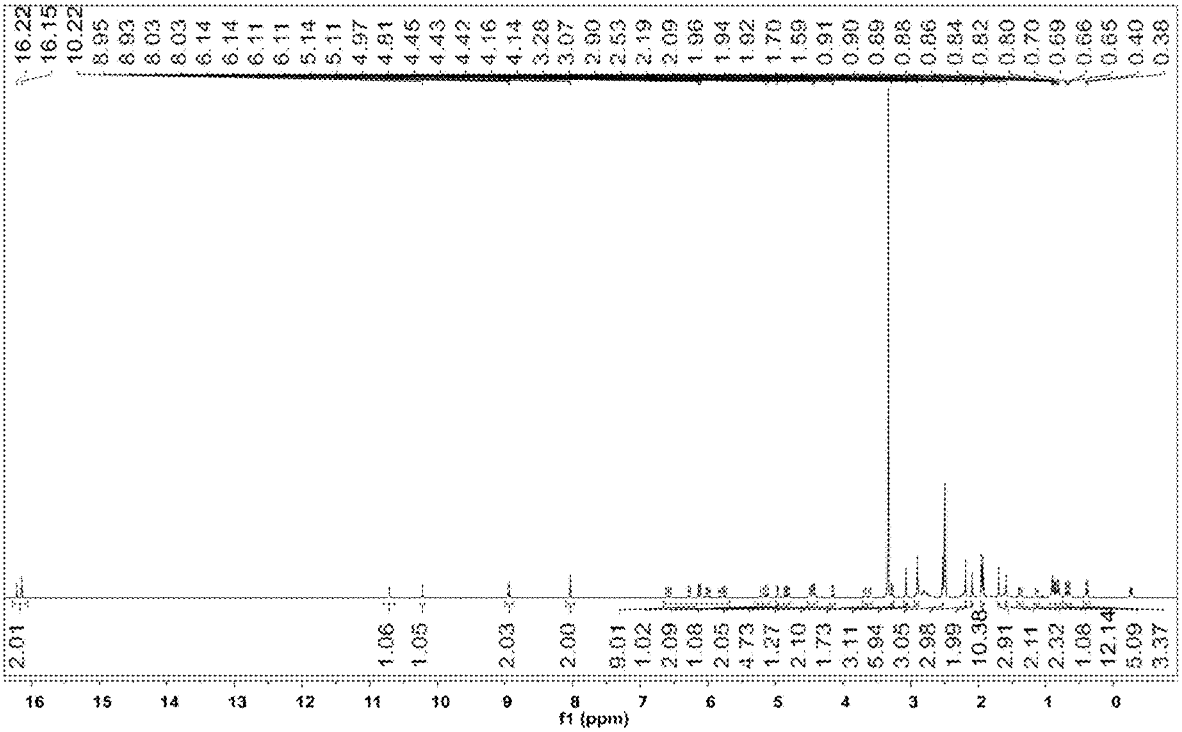
FIG. 5 shows the $^1$H NMR spectrum of the crystal form A of the present application.
Figure 6A:
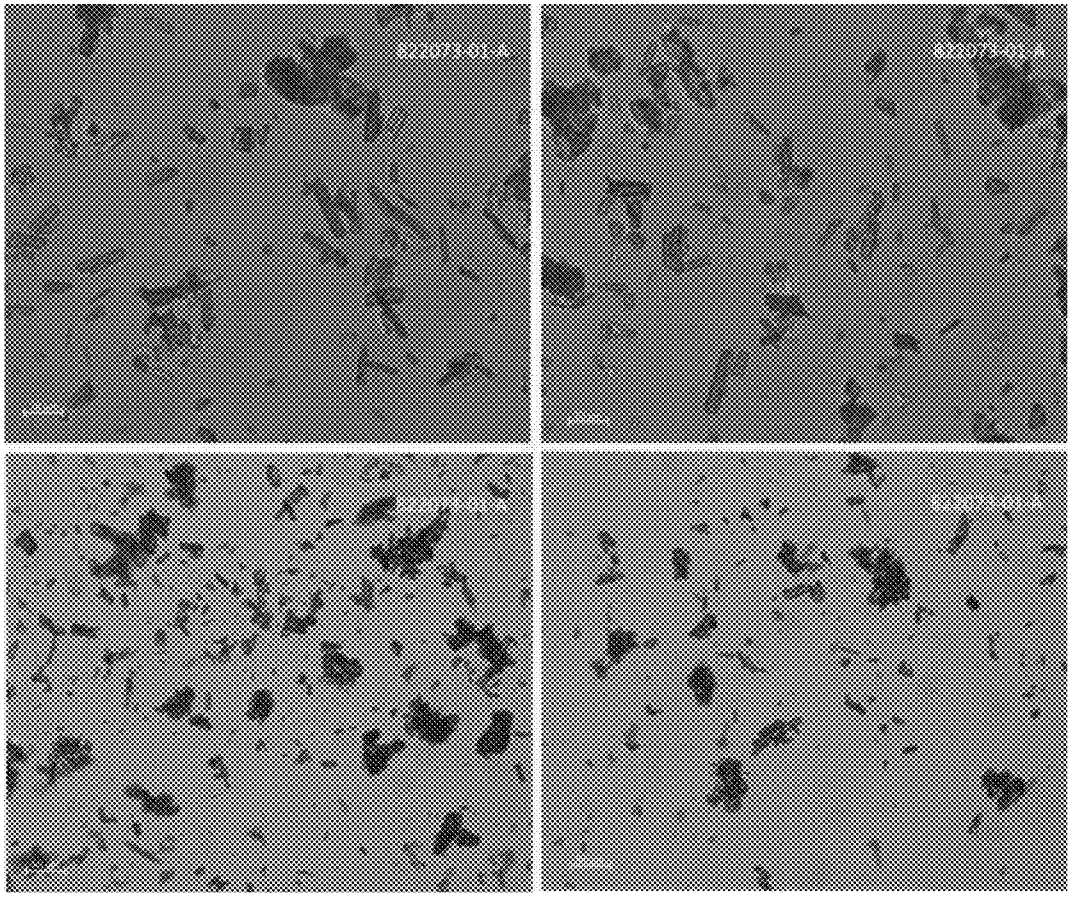
FIGS. 6A-6B show the PLM observation results of the crystal form A of the present application.
Figure 6B:
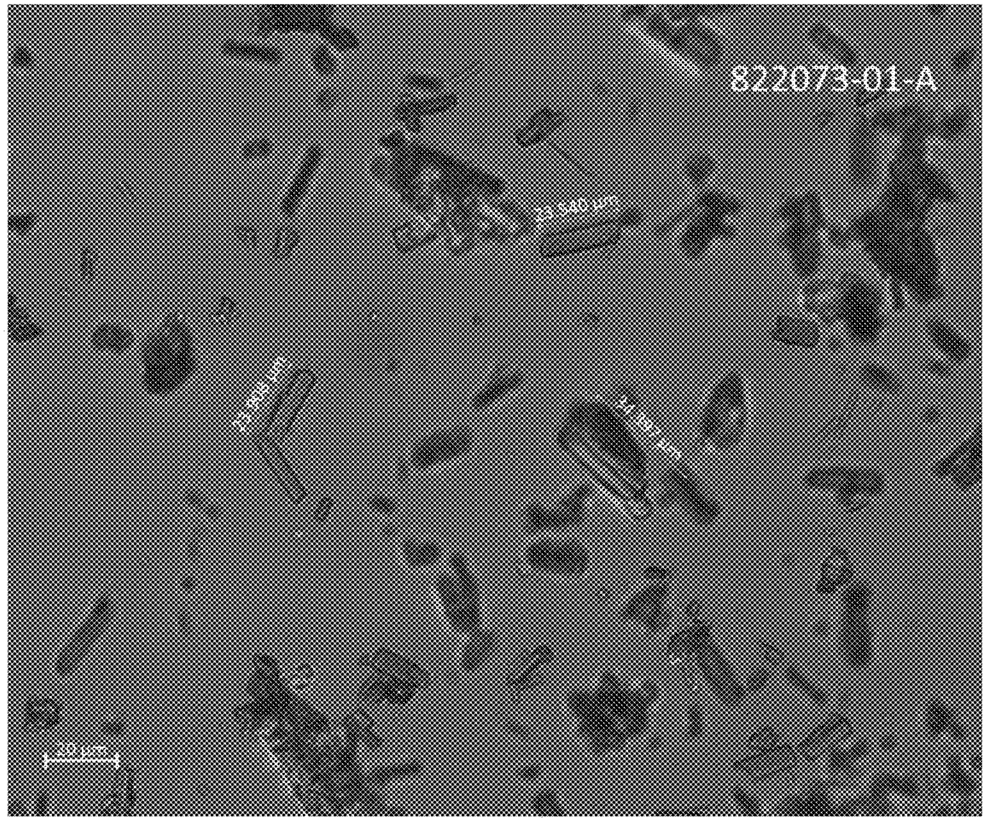

Preparation and Characterization of Crystal Form A and Crystal Form B of the Present Application (1) Preparation of Crystal Form A 40.05 g of the crude compound of formula (I) was weighed and mixed with methanol or ethanol of 5 folds by mass, and the mixture was stirred at 25° C. for 30 minutes. At this point, a visible solid precipitate was observed. The mixture was stirred for another 2-3 hours, followed by filtration. The wet cake was washed with 80 mL of methanol or ethanol. The wet cake was dried under vacuum at 42° C. for 52 hours to finally obtain 36.12 g of crystal form product, with a yield of about 67.9%. The purity was determined by high-performance liquid chromatography (HPLC) to be 99.6%. This crystal form product was sampled and subjected to X-ray powder diffraction (XRPD) detection, thermogravimetric analysis (TGA), differential scanning calorimetry (DSC) analysis, solution hydrogen nuclear magnetic resonance (Solution $^1$H NMR) analysis, and polarized light microscopy (PLM) observation. The results are shown in FIG. 1, Table 1, FIGS. 2A-2B, FIG. 5, and FIGS. 6A-6B. From the characterization results of the crystal form A, the XRPD diffraction peaks (FIG. 1) indicated high crystallinity of the crystal form A. No solvent residues were observed by $^1$H NMR (FIG. 5), suggesting that the crystal form A is an anhydrate and/or a nonsolvate. The TGA/DSC results (FIGS. 2A-2B) showed a weight loss of 1.36% when the sample of the crystal form A was heated to 150° C., and 1 endothermic peak was observed at 169.3° C. (peak temperature). The PLM results (FIGS. 6A-6B) showed that the sample was in a flat rod shape and had a particle size of about 10-50 μm.

TABLE 1

X-ray powder diffraction data for crystal form A

| Pos. [°2θ] | Height [cts] | FWHM Left [°2θ] | Rel. Int. [%] |
|---|---|---|---|
| 3.3657 | 30.3 | 0.3582 | 1.31 |
| 5.2778 | 1047.08 | 0.1023 | 45.28 |
| 5.8026 | 51.49 | 0.1023 | 2.23 |
| 7.1684 | 1933.77 | 0.1279 | 83.63 |
| 8.1323 | 375.24 | 0.1023 | 16.23 |
| 8.5029 | 1281.46 | 0.1023 | 55.42 |
| 9.9473 | 394.83 | 0.1535 | 17.07 |
| 10.6631 | 1335.9 | 0.1279 | 57.77 |
| 11.0234 | 283.1 | 0.1023 | 12.24 |
| 11.4657 | 314.3 | 0.1535 | 13.59 |
| 11.8684 | 79.6 | 0.1279 | 3.44 |
| 12.6142 | 507.25 | 0.1279 | 21.94 |
| 12.8938 | 229.28 | 0.1279 | 9.92 |
| 13.2446 | 126.26 | 0.1023 | 5.46 |
| 13.5724 | 37.71 | 0.1023 | 1.63 |
| 14.3305 | 1456.46 | 0.1023 | 62.99 |
| 14.8272 | 824.77 | 0.1279 | 35.67 |
| 15.257 | 1177.53 | 0.1279 | 50.92 |
| 15.5141 | 852.5 | 0.1023 | 36.87 |
| 15.8374 | 2312.31 | 0.1535 | 100 |
| 16.5663 | 960.38 | 0.1279 | 41.53 |
| 17.3156 | 244.48 | 0.1535 | 10.57 |
| 17.9418 | 123.96 | 0.1791 | 5.36 |
| 18.3524 | 870.66 | 0.1535 | 37.65 |
| 18.5997 | 1302.22 | 0.1279 | 56.32 |
| 18.8687 | 452.03 | 0.1023 | 19.55 |
| 19.4931 | 398.23 | 0.1535 | 17.22 |
| 19.9708 | 830.56 | 0.1535 | 35.92 |
| 20.3273 | 269.08 | 0.1279 | 11.64 |
| 20.6373 | 248.67 | 0.2047 | 10.75 |
| 21.3782 | 192.03 | 0.1535 | 8.3 |

TABLE 1-continued

X-ray powder diffraction data for crystal form A

| Pos. [°2θ] | Height [cts] | FWHM Left [°2θ] | Rel. Int. [%] |
|---|---|---|---|
| 21.9722 | 517.19 | 0.1535 | 22.37 |
| 22.7326 | 276.38 | 0.1279 | 11.95 |
| 23.9256 | 79.58 | 0.4093 | 3.44 |
| 24.1078 | 113.95 | 0.1023 | 4.93 |
| 25.4594 | 307.1 | 0.307 | 13.28 |
| 26.3681 | 273.55 | 0.2047 | 11.83 |
| 28.0255 | 131.31 | 0.4605 | 5.68 |
| 28.7845 | 77.31 | 0.2047 | 3.34 |
| 29.2589 | 63.48 | 0.2047 | 2.75 |
| 30.8124 | 87.21 | 0.2558 | 3.77 |
| 31.3623 | 72.29 | 0.1535 | 3.13 |
| 32.7053 | 26.84 | 0.1535 | 1.16 |
| 33.4038 | 51.96 | 0.2047 | 2.25 |
| 34.6447 | 19.48 | 0.614 | 0.84 |
| 37.3142 | 25.86 | 0.307 | 1.12 |
| 38.1487 | 35.37 | 0.1023 | 1.53 |
| 39.2101 | 15.07 | 0.2558 | 0.65 |

(2) Preparation of Crystal Forms C1-C3

Figure 9A:
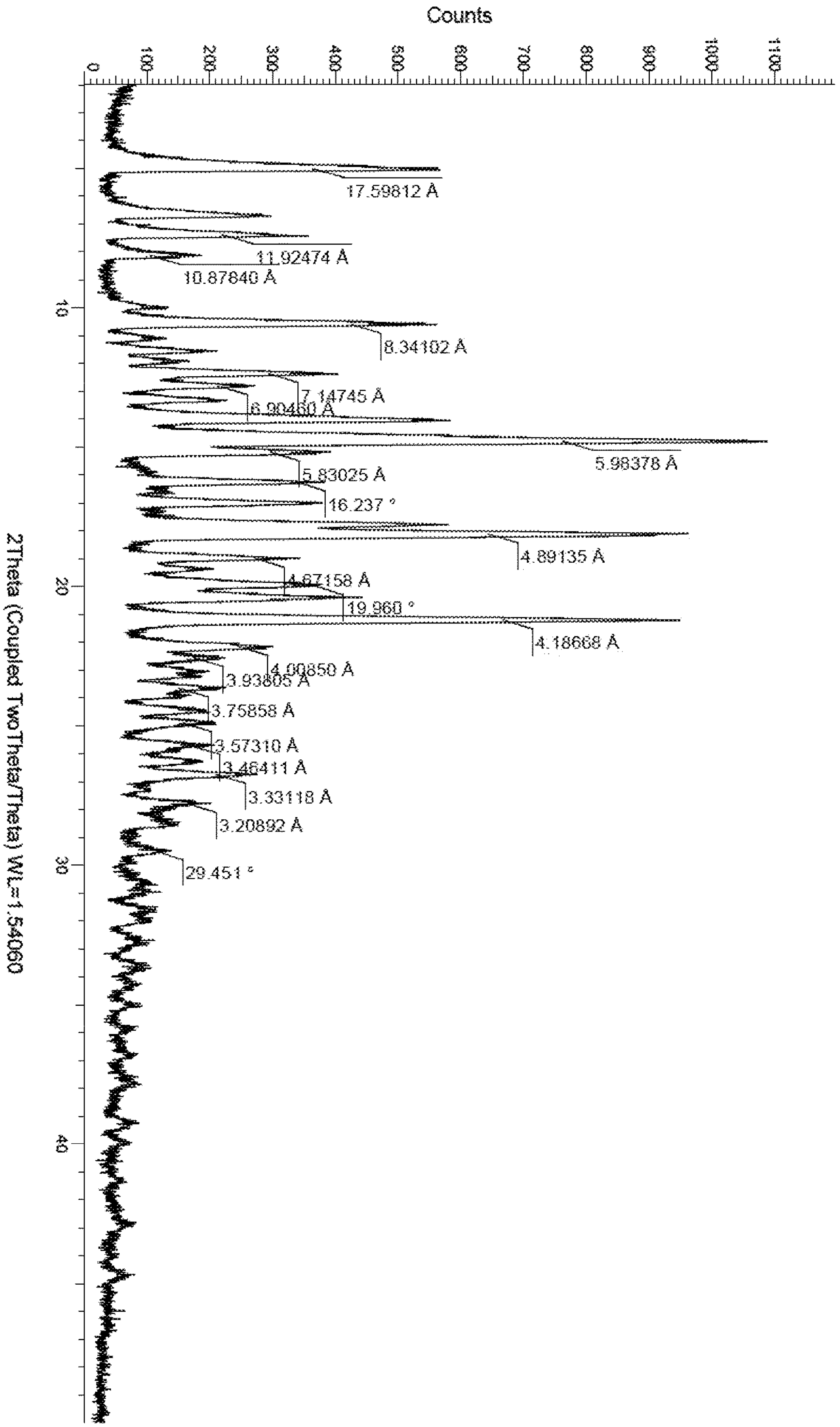
FIGS. 9A-9C show the XRPD patterns of crystal forms C1, C2, and C3 of the present application.
Figure 9B:
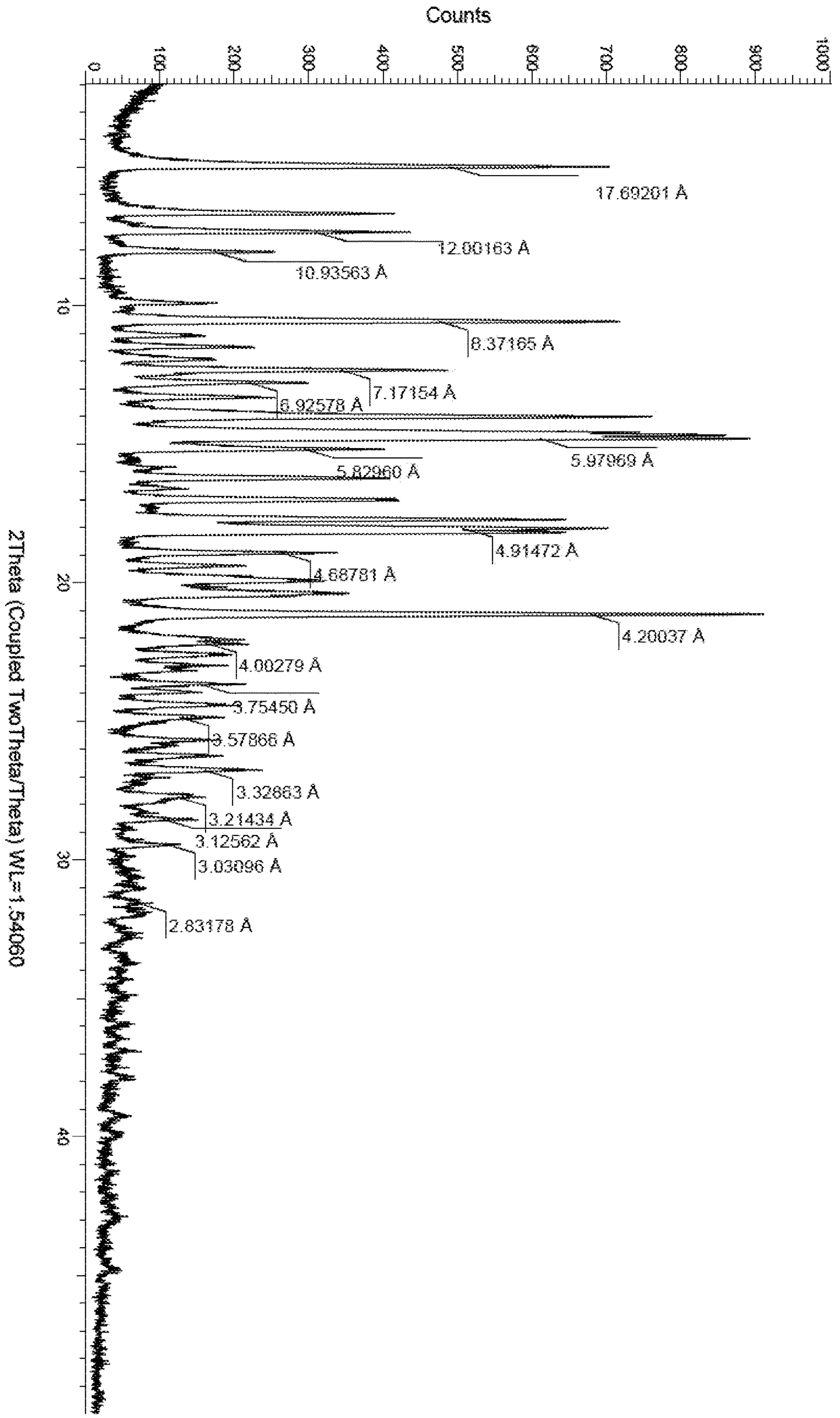
Figure 9C:
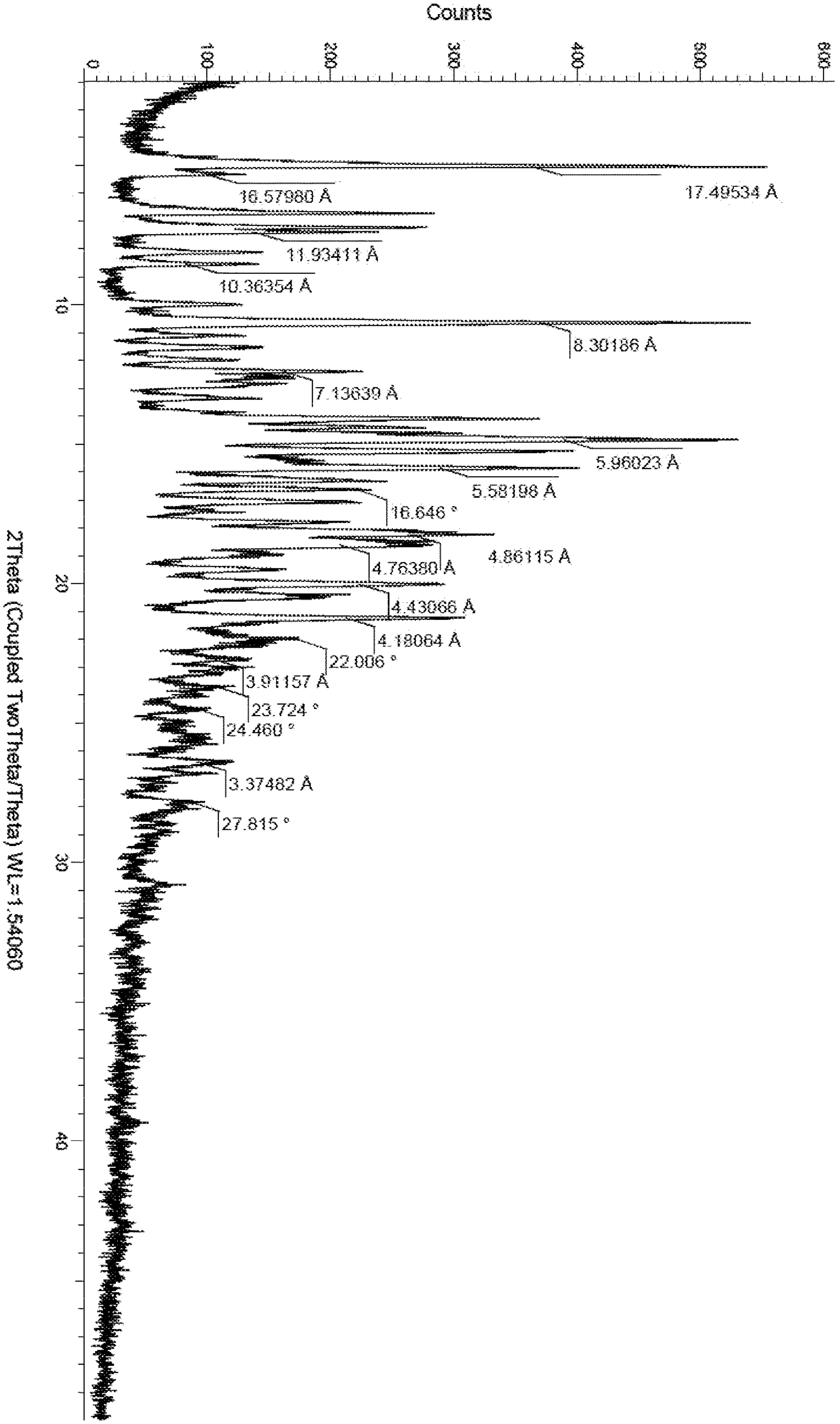
Figure 9D:
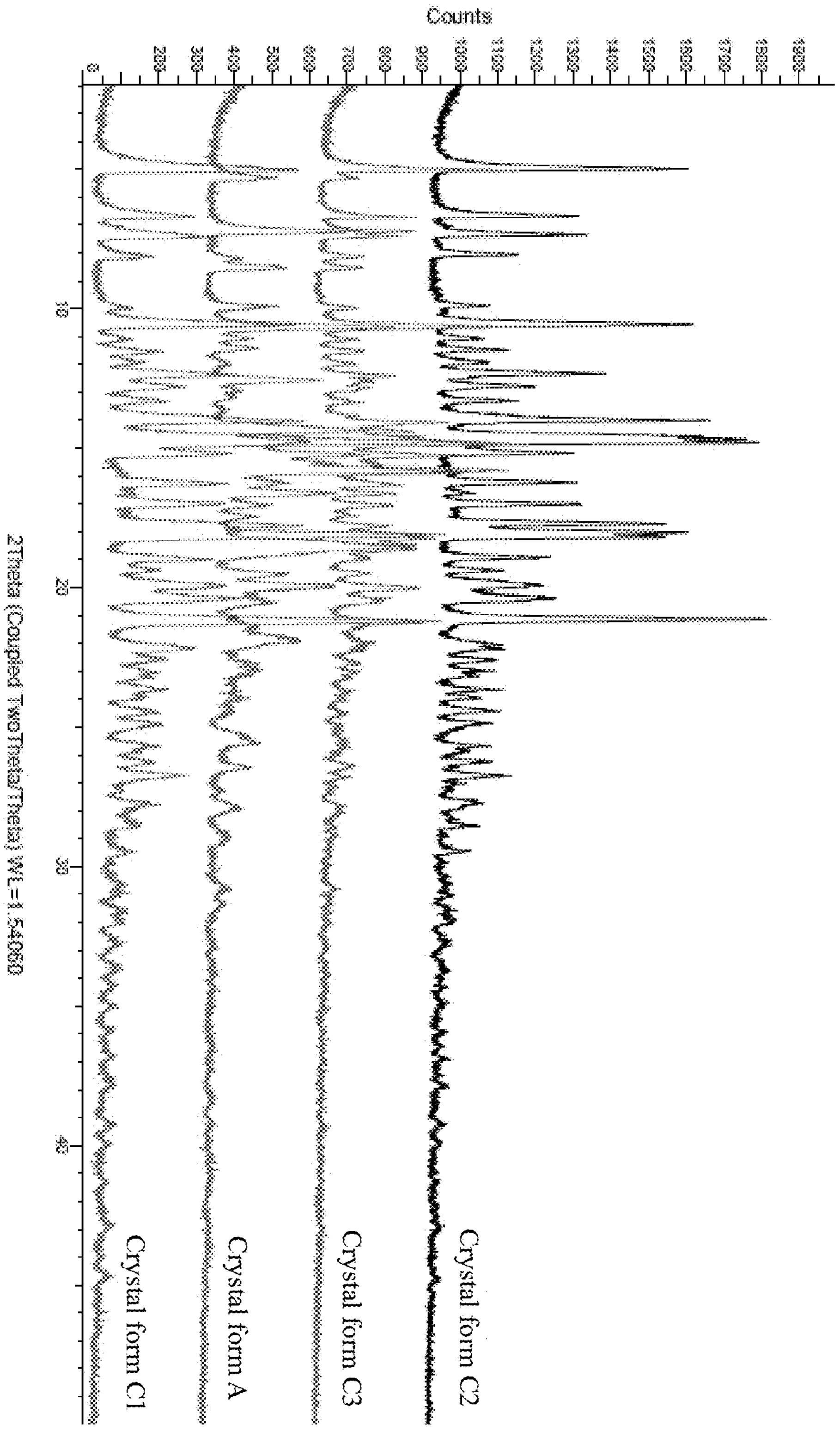
FIG. 9D shows the XRPD patterns of crystal forms C1, C2, and C3 after drying.

40.05 g of the crude compound of formula (I) was weighed and mixed with ethanol of 5 folds by mass, and the mixture was stirred at 25° C. for 30 minutes. At this point, a visible solid precipitate was observed. The mixture was stirred for another 2-3 hours, followed by filtration. The wet cake was washed with 80 mL of ethanol. Three solvate crystal forms, C1, C2, and C3, with different structures were detected in the undried wet product of the compound of formula (I) formed in ethanol. Their XRPD results are shown in FIGS. 9A-9C, Table 2-1, Table 2-2, and Table 2-3. However, after drying, crystal forms C1, C2, and C3 were all converted to crystal form A. The XRPD results are shown in FIG. 9D.

TABLE 2-1

X-ray powder diffraction data for crystal form C1

| Index | Angle | Rel. Intensity | Position |
|---|---|---|---|
| 1 | 5.017° | 47.90% | 5.017 |
| 2 | 6.708° | 25.60% | 6.708 |
| 3 | 7.407° | 26.70% | 7.407 |
| 4 | 8.121° | 10.30% | 8.121 |
| 5 | 9.970° | 7.20% | 9.97 |
| 6 | 10.598° | 55.00% | 10.598 |
| 7 | 11.088° | 5.90% | 11.088 |
| 8 | 11.551° | 15.10% | 11.551 |
| 9 | 11.916° | 11.70% | 11.916 |
| 10 | 12.374° | 33.00% | 12.374 |
| 11 | 12.811° | 20.70% | 12.811 |
| 12 | 13.326° | 15.60% | 13.326 |
| 13 | 14.052° | 51.10% | 14.052 |
| 14 | 14.793° | 100.00% | 14.793 |
| 15 | 15.184° | 32.30% | 15.184 |
| 16 | 16.275° | 31.30% | 16.275 |
| 17 | 16.978° | 29.30% | 16.978 |
| 18 | 17.780° | 51.50% | 17.78 |
| 19 | 18.122° | 82.50% | 18.122 |
| 20 | 18.982° | 28.20% | 18.982 |
| 21 | 19.368° | 10.60% | 19.368 |
| 22 | 19.946° | 29.80% | 19.946 |
| 23 | 20.394° | 30.40% | 20.394 |
| 24 | 21.204° | 85.60% | 21.204 |
| 25 | 22.159° | 23.90% | 22.159 |
| 26 | 22.560° | 13.40% | 22.56 |
| 27 | 23.653° | 10.50% | 23.653 |
| 28 | 24.507° | 11.20% | 24.507 |
| 29 | 24.899° | 12.10% | 24.899 |
| 30 | 25.696° | 14.10% | 25.696 |
| 31 | 26.276° | 11.50% | 26.276 |
| 32 | 26.740° | 19.90% | 26.74 |

TABLE 2-1-continued

X-ray powder diffraction data for crystal form C1

| Index | Angle | Rel. Intensity | Position |
|---|---|---|---|
| 33 | 27.779° | 13.60% | 27.779 |
| 34 | 28.560° | 11.10% | 28.56 |
| 35 | 29.545° | 8.40% | 29.545 |

TABLE 2-2

X-ray powder diffraction data for crystal form C2

| Index | Angle | Rel. Intensity | Position |
|---|---|---|---|
| 1 | 4.991° | 73.70% | 4.991 |
| 2 | 6.682° | 40.00% | 6.682 |
| 3 | 7.360° | 44.90% | 7.36 |
| 4 | 8.078° | 23.60% | 8.078 |
| 5 | 9.918° | 11.90% | 9.918 |
| 6 | 10.559° | 69.90% | 10.559 |
| 7 | 11.070° | 8.50% | 11.07 |
| 8 | 11.494° | 18.00% | 11.494 |
| 9 | 11.926° | 14.20% | 11.926 |
| 10 | 12.332° | 47.20% | 12.332 |
| 11 | 12.772° | 26.60% | 12.772 |
| 12 | 13.313° | 21.80% | 13.313 |
| 13 | 14.006° | 77.50% | 14.006 |
| 14 | 14.803° | 88.80% | 14.803 |
| 15 | 15.186° | 38.30% | 15.186 |
| 16 | 16.235° | 40.70% | 16.235 |
| 17 | 16.600° | 8.00% | 16.6 |
| 18 | 17.025° | 36.90% | 17.025 |
| 19 | 17.722° | 62.80% | 17.722 |
| 20 | 18.035° | 72.50% | 18.035 |
| 21 | 18.915° | 33.00% | 18.915 |
| 22 | 19.388° | 17.70% | 19.388 |
| 23 | 19.916° | 25.20% | 19.916 |
| 24 | 20.374° | 31.30% | 20.374 |
| 25 | 21.134° | 100.00% | 21.134 |
| 26 | 22.156° | 18.40% | 22.156 |
| 27 | 22.598° | 16.40% | 22.598 |
| 28 | 23.018° | 16.90% | 23.018 |
| 29 | 23.679° | 16.00% | 23.679 |
| 30 | 23.953° | 10.80% | 23.953 |
| 31 | 24.415° | 13.10% | 24.415 |
| 32 | 24.860° | 13.30% | 24.86 |
| 33 | 25.692° | 17.10% | 25.692 |
| 34 | 26.245° | 16.10% | 26.245 |
| 35 | 26.761° | 18.00% | 26.761 |
| 36 | 27.731° | 12.00% | 27.731 |
| 37 | 28.535° | 9.30% | 28.535 |
| 38 | 29.446° | 11.20% | 29.446 |

TABLE 2-3

X-ray powder diffraction data for crystal form C3

| Index | Angle | Rel. Intensity | Position |
|---|---|---|---|
| 1 | 5.047° | 97.00% | 5.047 |
| 2 | 5.326° | 19.50% | 5.326 |
| 3 | 6.727° | 51.10% | 6.727 |
| 4 | 7.237° | 44.70% | 7.237 |
| 5 | 7.402° | 32.00% | 7.402 |
| 6 | 8.131° | 22.50% | 8.131 |
| 7 | 8.525° | 18.20% | 8.525 |
| 8 | 9.987° | 19.70% | 9.987 |
| 9 | 10.648° | 100.00% | 10.648 |
| 10 | 11.102° | 17.20% | 11.102 |
| 11 | 11.526° | 16.50% | 11.526 |
| 12 | 11.992° | 17.20% | 11.992 |
| 13 | 12.393° | 34.90% | 12.393 |
| 14 | 12.849° | 22.00% | 12.849 |
| 15 | 13.358° | 18.60% | 13.358 |
| 16 | 14.102° | 66.50% | 14.102 |

TABLE 2-3-continued

X-ray powder diffraction data for crystal form C3

| Index | Angle | Rel. Intensity | Position |
|---|---|---|---|
| 17 | 14.398° | 42.10% | 14.398 |
| 18 | 14.851° | 96.40% | 14.851 |
| 19 | 15.256° | 66.20% | 15.256 |
| 20 | 15.864° | 65.60% | 15.864 |
| 21 | 16.318° | 32.40% | 16.318 |
| 22 | 16.635° | 35.90% | 16.635 |
| 23 | 17.061° | 29.20% | 17.061 |
| 24 | 17.785° | 31.40% | 17.785 |
| 25 | 18.235° | 58.90% | 18.235 |
| 26 | 18.611° | 42.10% | 18.611 |
| 27 | 18.938° | 16.00% | 18.938 |
| 28 | 19.492° | 19.30% | 19.492 |
| 29 | 20.024° | 46.60% | 20.024 |
| 30 | 20.470° | 23.30% | 20.47 |
| 31 | 21.235° | 42.90% | 21.235 |
| 32 | 21.992° | 26.90% | 21.992 |
| 33 | 22.715° | 11.60% | 22.715 |
| 34 | 23.059° | 17.00% | 23.059 |
| 35 | 23.716° | 16.00% | 23.716 |
| 36 | 24.496° | 6.90% | 24.496 |
| 37 | 26.388° | 13.40% | 26.388 |

(3) Preparation of Crystal Form B

Figure 3:
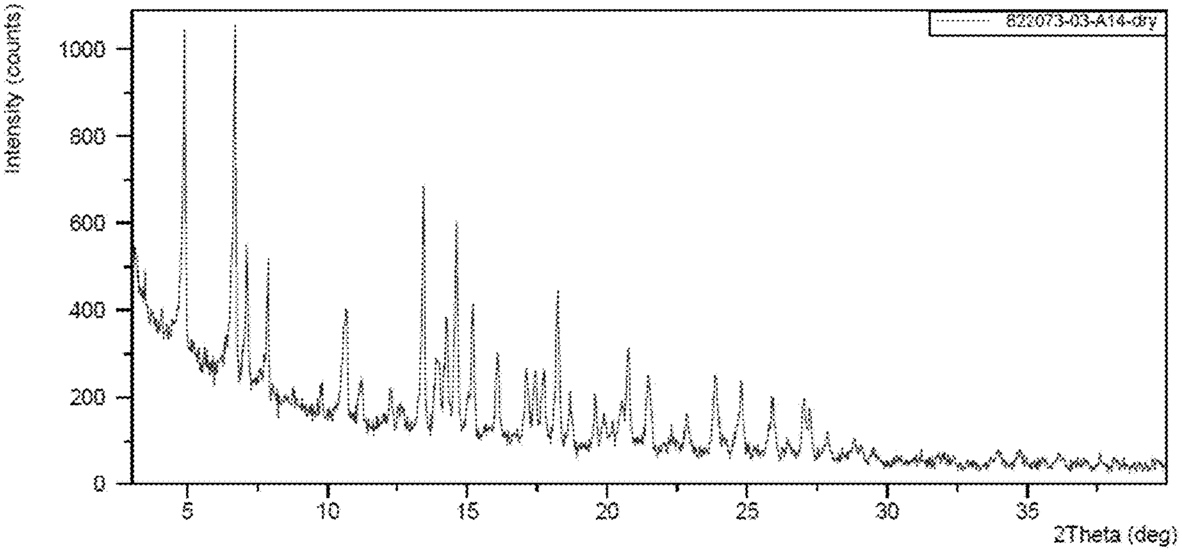
FIG. 3 shows the XRPD pattern of the crystal form B of the present application.
Figure 4A:
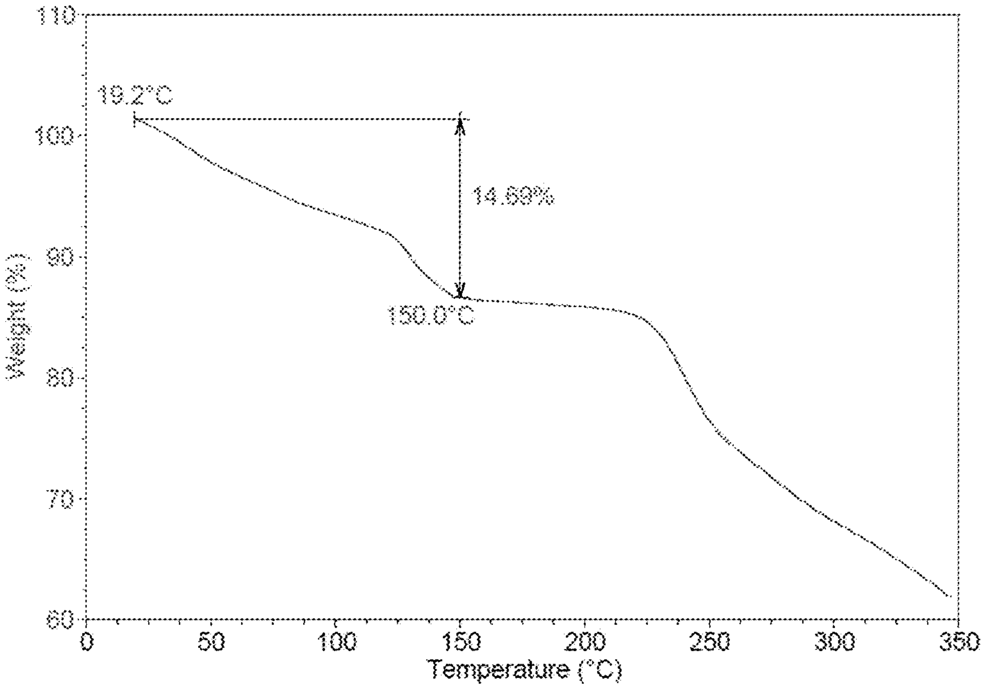
FIGS. 4A-4B show the TGA plot and the DSC plot of the crystal form B of the present application.
Figure 4B:
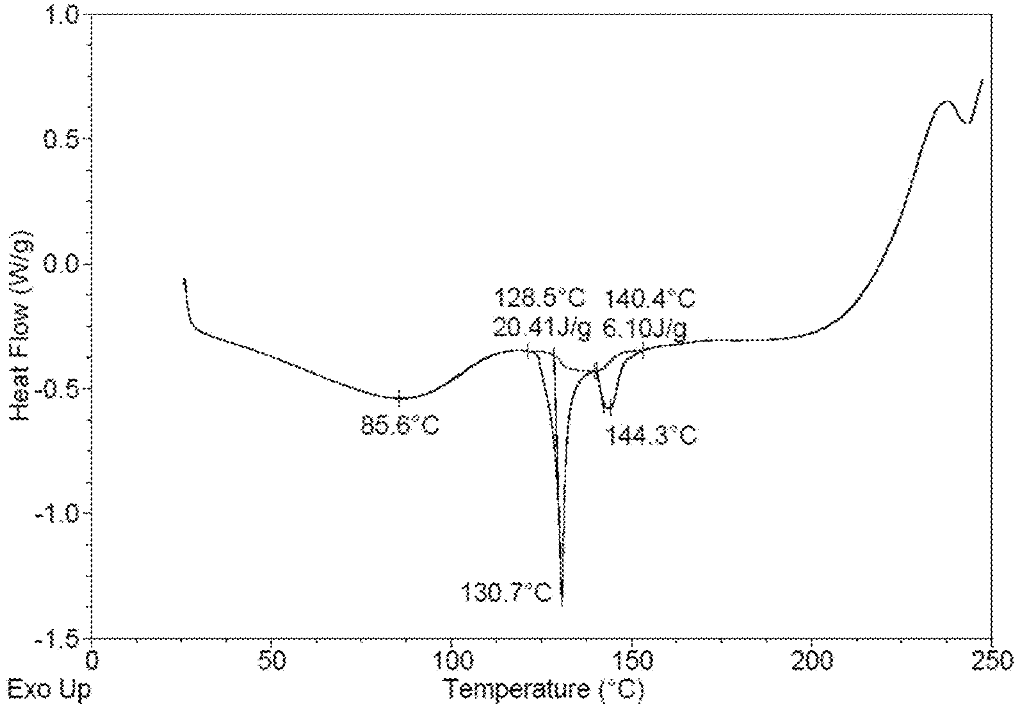
Figure 7A:
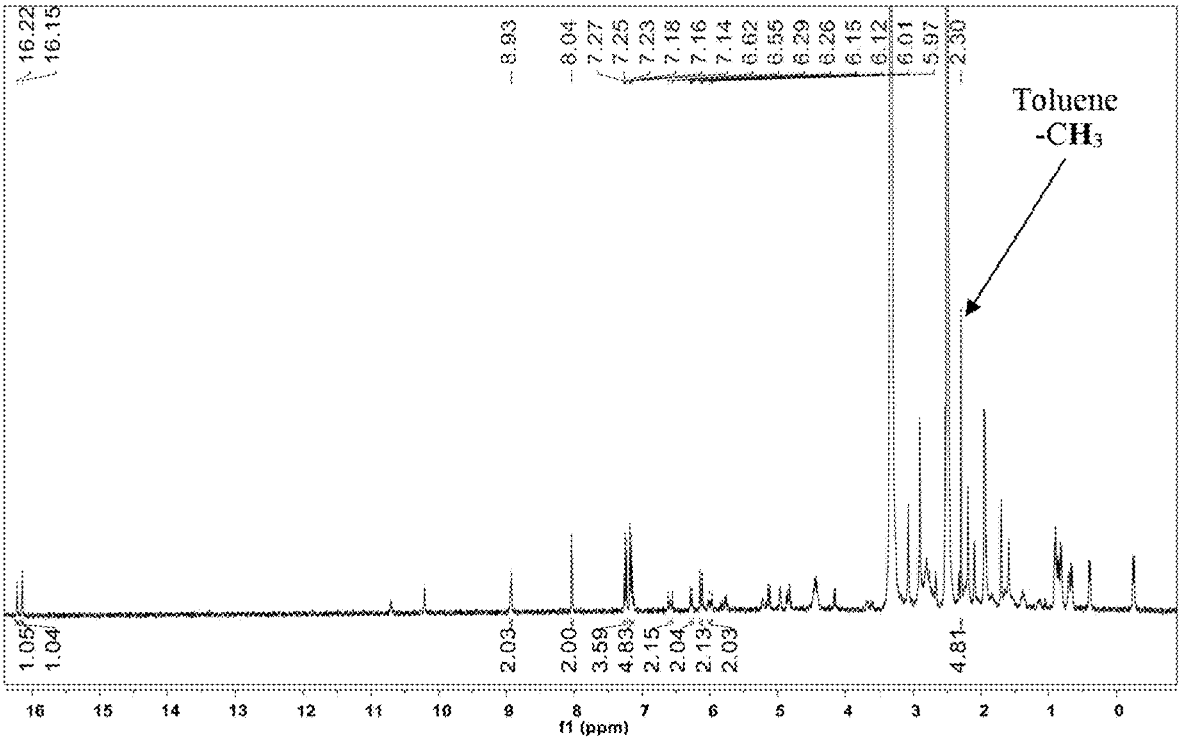
FIGS. 7A-7C show the $^1$H NMR spectra of the crystal form B of the present application from the beginning, and after being heated to 115° C. and 140° C., respectively.
Figure 7B:
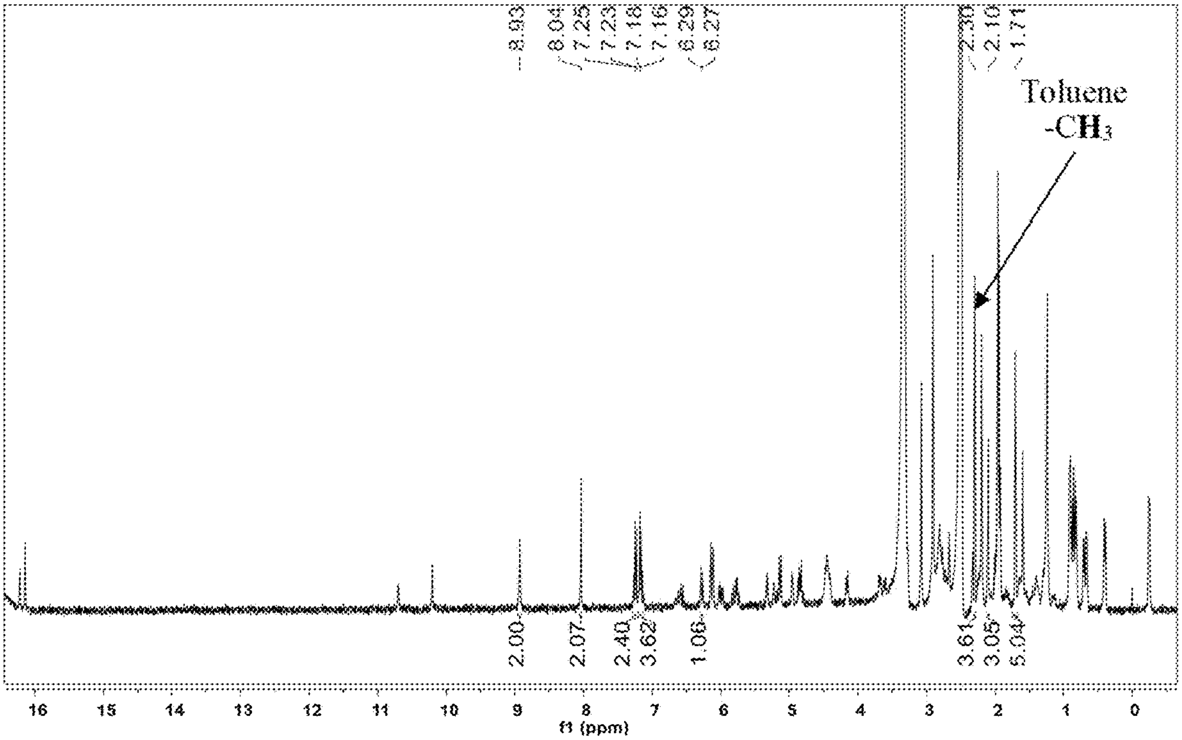
Figure 7C:
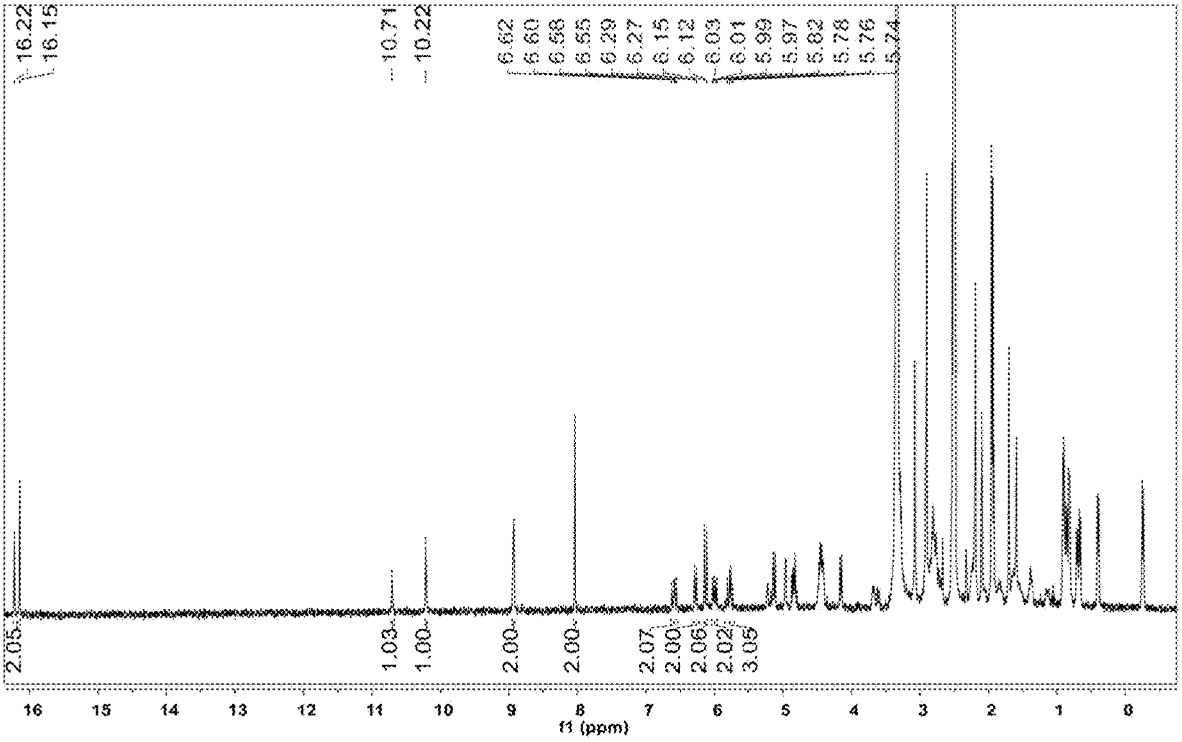
Figure 8:
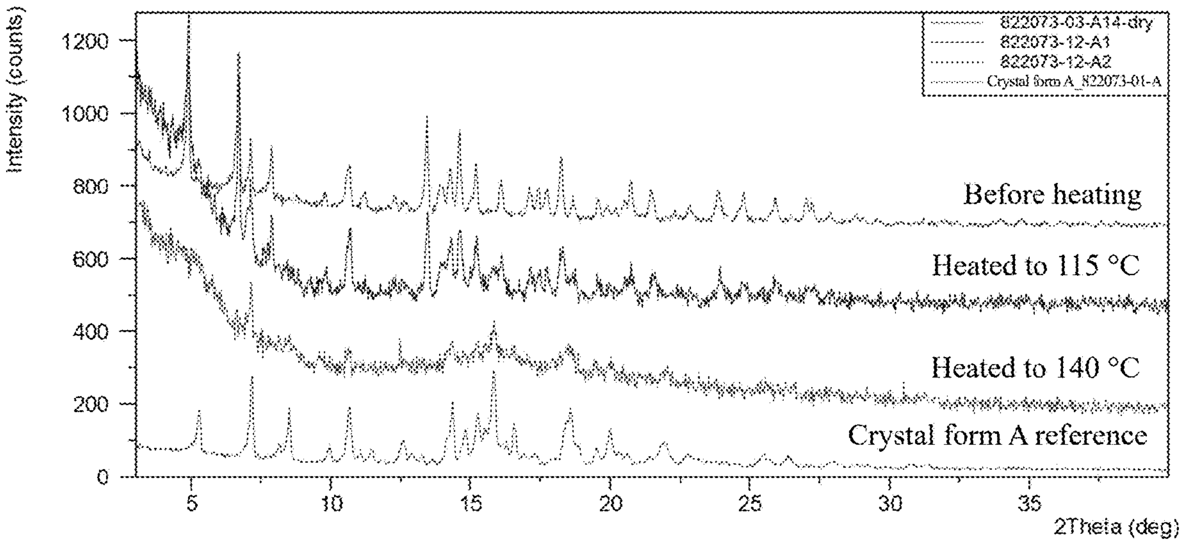
FIG. 8 shows the results from the comparative overlay of the XRPD patterns of the crystal form B of the present application before and after heating.

The crystal form B was obtained by shaking the crystal form product (crystal form A) from (1) in this example in a toluene solvent at room temperature for 24 hours, and the crystal form remained unchanged after air-drying at room temperature for 24 hours. The XRPD results are shown in FIG. 3 and Table 3. The TGA/DSC results (FIGS. 4A-4B) showed that the sample of the crystal form B had a weight loss of 9.33% when heated to 120° C., and a further weight loss of 5.36% when heated to 150° C. Furthermore, the sample had 3 endothermic peaks at 85.6° C., 130.7° C., and 144.3° C. (peak temperatures). The $^{1}$H NMR results (FIG. 7A) showed that the molar ratio of the residual toluene solvent to API in the sample was 1.6 (13.5 wt %). To further investigate the substantial TGA weight loss of the crystal form B sample, a heating experiment was performed on it. The XRPD results (FIG. 8) showed that the crystal form of the crystal form B sample remained unchanged after heating to 115° C. and cooling to room temperature, while the crystal form B sample was converted to crystal form A after heating to 140° C. and cooling to room temperature, but with poor crystallinity. The 1H NMR results (FIGS. 7B and 7C) showed that the molar ratio of the residual toluene solvent to API was 1.2 (10.5 wt %) after the sample was heated to 115° C. and cooled to room temperature, and no toluene solvent residue was detected after the sample was heated to 140° C. and cooled to room temperature. Due to the crystal form conversion upon sample heating, combined with the substantial TGA weight loss and the solvent residue indicated by the nuclear magnetic resonance results after heating, it can be inferred that crystal form B is a toluene solvate.

TABLE 3

X-ray powder diffraction data for crystal form B

| Pos. [°2θ] | Height [cts] | FWHM Left [°2θ] | Rel. Int. [%] |
|---|---|---|---|
| 3.1408 | 31.46 | 0.1535 | 4.43 |
| 4.069 | 14.85 | 0.1535 | 2.09 |
| 4.8938 | 709.54 | 0.1023 | 100 |
| 6.6737 | 646.71 | 0.1535 | 91.14 |
| 7.1183 | 289.64 | 0.1023 | 40.82 |
| 7.8408 | 250.45 | 0.1023 | 35.3 |
| 8.8217 | 16.72 | 0.1535 | 2.36 |

TABLE 3-continued

| X-ray powder diffraction data for crystal form B | | | |
|---|---|---|---|
| Pos. [°2θ] | Height [cts] | FWHM Left [°2θ] | Rel. Int. [%] |
| 9.7557 | 62.41 | 0.1279 | 8.8 |
| 10.6733 | 260.93 | 0.1791 | 36.77 |
| 11.2025 | 103.51 | 0.1023 | 14.59 |
| 12.2499 | 88.69 | 0.1535 | 12.5 |
| 12.5896 | 41.49 | 0.2047 | 5.85 |
| 13.4082 | 562.89 | 0.1023 | 79.33 |
| 13.9775 | 160.98 | 0.2303 | 22.69 |
| 14.2486 | 259.05 | 0.1279 | 36.51 |
| 14.6167 | 457.24 | 0.1023 | 64.44 |
| 15.1866 | 287.97 | 0.1279 | 40.58 |
| 16.0731 | 178.22 | 0.1279 | 25.12 |
| 17.0986 | 152.69 | 0.1535 | 21.52 |
| 17.4133 | 158.87 | 0.1023 | 22.39 |
| 17.737 | 152.63 | 0.1535 | 21.51 |
| 18.2286 | 342.11 | 0.1279 | 48.22 |
| 18.6621 | 119.58 | 0.1535 | 16.85 |
| 19.5884 | 103.08 | 0.1279 | 14.53 |
| 19.9033 | 61.86 | 0.1535 | 8.72 |
| 20.7345 | 223.06 | 0.1023 | 31.44 |
| 21.4057 | 137.54 | 0.1279 | 19.38 |
| 22.0037 | 12.45 | 0.1023 | 1.75 |
| 22.268 | 30.42 | 0.2047 | 4.29 |
| 22.816 | 85.96 | 0.1279 | 12.11 |
| 23.8422 | 179.65 | 0.1279 | 25.32 |
| 24.7692 | 155.41 | 0.1023 | 21.9 |
| 25.9104 | 117.85 | 0.1279 | 16.61 |
| 26.4794 | 34.34 | 0.2558 | 4.84 |
| 27.0011 | 130.65 | 0.1279 | 18.41 |
| 27.8705 | 54.36 | 0.2047 | 7.66 |
| 28.791 | 47 | 0.1535 | 6.62 |
| 29.4778 | 23.81 | 0.2047 | 3.36 |
| 30.4067 | 6.19 | 0.2558 | 0.87 |
| 33.9181 | 29.02 | 0.4093 | 4.09 |
| 34.6769 | 28.83 | 0.2047 | 4.06 |
| 35.6236 | 14 | 0.2047 | 1.97 |
| 36.1772 | 22.3 | 0.307 | 3.14 |
| 38.152 | 13.34 | 0.1535 | 1.88 |

Example 2

Evaluation of Crystal Form A of the Present Application (1) Hygroscopicity Test (Dynamic Vapor Sorption Test or DVS)

Figure 10:
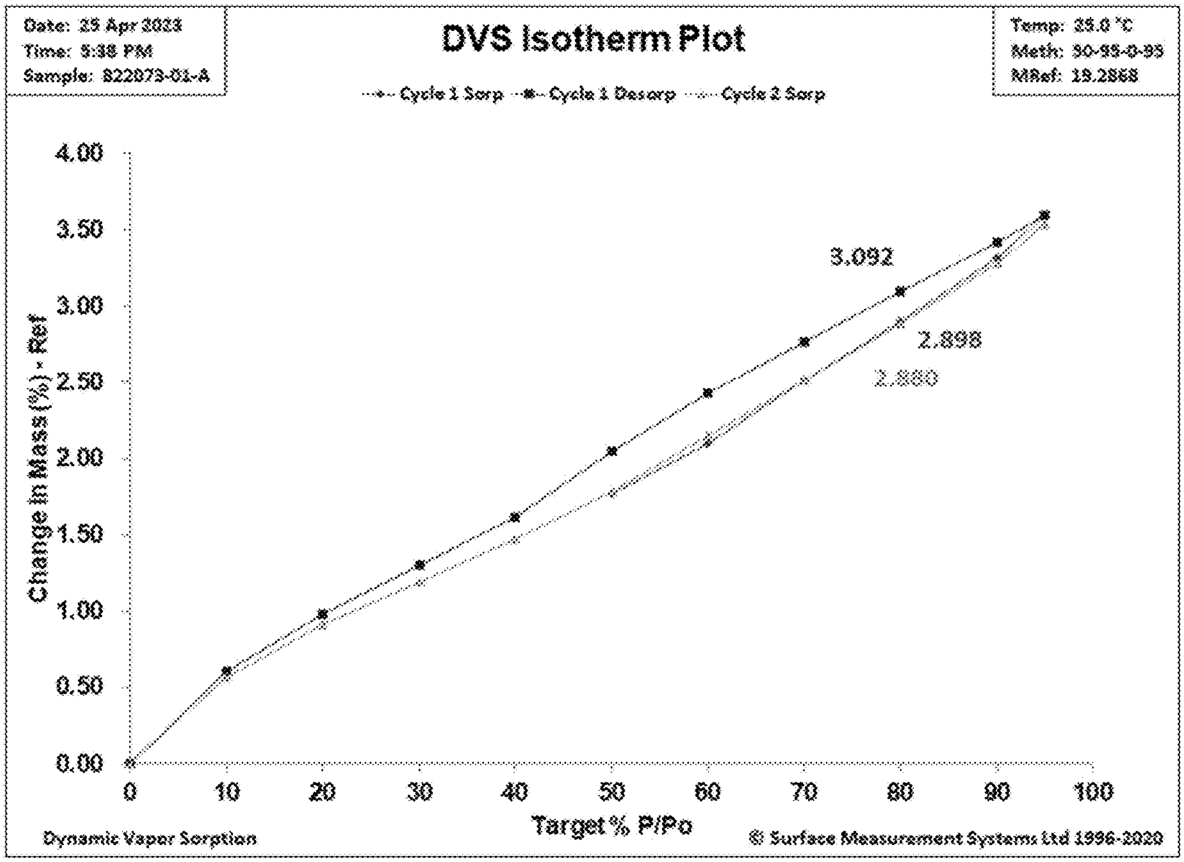
FIG. 10 shows the analysis results from the DVS experiment of the crystal form A of the present application.
Figure 11:
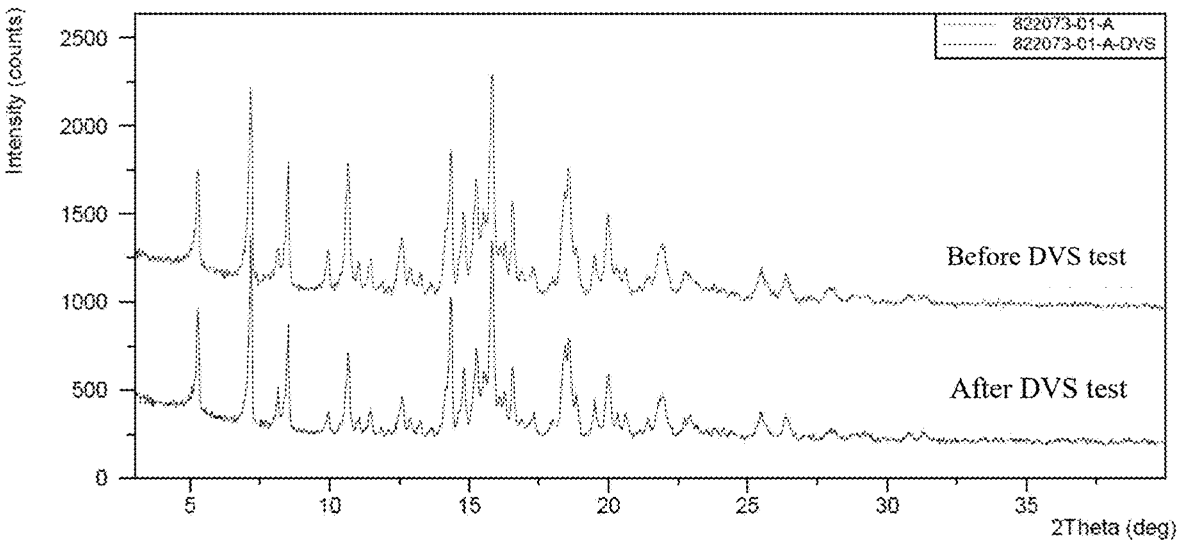
FIG. 11 shows the results from the comparative overlay of the XRPD patterns of the crystal form A of the present application before and after the DVS test.

DVS profiles were acquired on SMS (Surface Measurement Systems) DVS Intrinsic and DVS Intrinsic plus. The relative humidity at 25° C. was calibrated using the deliquescence points of LiCl, $Mg(NO_3)_2$, and KCl. The DVS results (FIG. 10) showed that the sample of the crystal form A exhibited a moisture uptake of 2.880% at 25° C./80% RH, indicating hygroscopicity. Under the same testing conditions, the amorphous form had a hygroscopicity result of 5.941%, demonstrating that the hygroscopicity of the crystal form A is superior to that of the amorphous form. Furthermore, the XRPD results of the crystal form A before and after the DVS test (FIG. 11) showed no crystal form conversion in its sample, indicating good stability of the crystal form A. In contrast, the crystal forms B, C1, C2, and C3 exhibited poor crystal form stability and were all converted to crystal form A after heating or drying.

(2) Solid Stability

Figure 12:
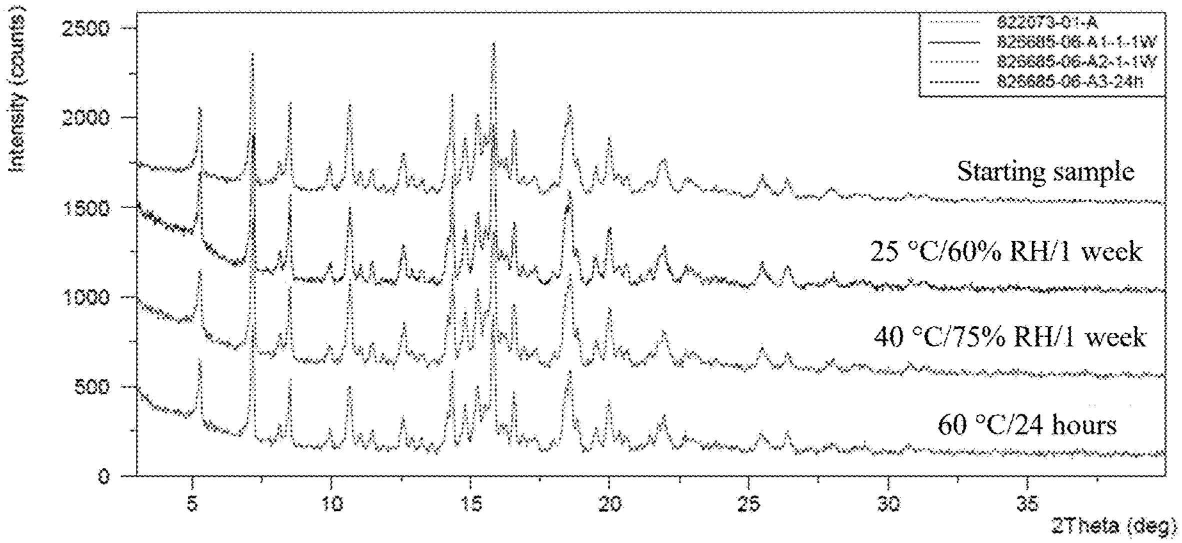
FIG. 12 shows the results from the comparative overlay of the XRPD patterns of the crystal form A of the present application in the solid stability evaluation.
Figure 13:
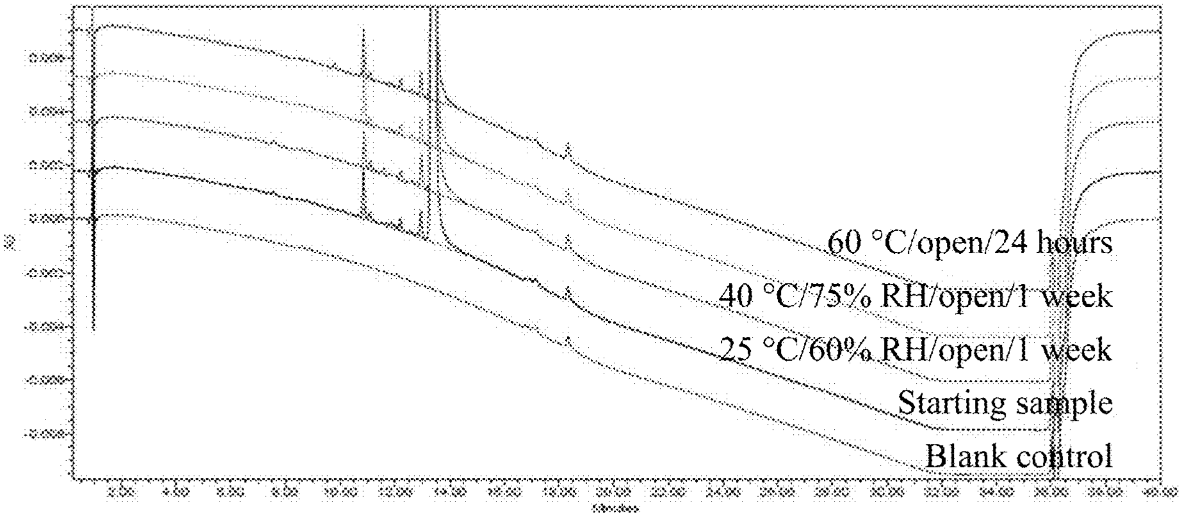
FIG. 13 shows the results from the comparative overlay of the HPLC chromatograms of the crystal form A of the present application in the solid stability evaluation.

The crystal form A was left to stand open at 60° C. for 24 hours, and at 25° C./60% RH and 40° C./75% RH for 1 week. The physical and chemical stability of the samples was detected by XRPD and HPLC. The stability evaluation results are summarized in Table 4, the XRPD results are shown in FIG. 12, and the HPLC results are shown in Table 5 and FIG. 13. The results showed that the samples of the crystal form A, after being placed under the above 3 conditions, exhibited no significant change in purity and no crystal form conversion.

TABLE 4

| Summary of solid stability evaluation of crystal form A | | | | |
|---|---|---|---|---|
| Starting sample | Conditions | Time | HPLC purity (area %) | Change in crystal form |
| Crystal form A (prepared in Example 1(1)) | Starting sample | N.A. | 99.32 | N.A. |
| | 60° C. | 24 hours | 99.33 | No |
| | 25° C./60° C. RH | 1 week | 99.45 | No |
| | 40° C./75° C. RH | 1 week | 99.29 | No |

TABLE 5

| HPLC impurity summary of solid stability samples of crystal form A | | | | | |
|---|---|---|---|---|---|
| # Peak | RRT | Starting sample | 60° C./open/ 24 hours | 25° C./60% RH/ Open/1 week | 40° C./75% RH/ Open/1 week |
| 1 | 0.81 | 0.29 | 0.30 | 0.18 | 0.38 |
| 2 | 0.83 | 0.07 | 0.07 | 0.06 | 0.06 |
| 3 | 0.87 | 0.08 | 0.06 | 0.05 | 0.05 |
| 4 | 0.91 | 0.07 | 0.07 | 0.06 | 0.06 |
| 5 | 0.97 | 0.17 | 0.17 | 0.19 | 0.16 |
| 6 | 1.00 | 99.32 | 99.33 | 99.45 | 99.29 |

(3) Purification/Impurity Removal Effect

In this example, the effects of the crystal form A sample and the amorphous form sample of the compound of formula (I) in the purification and impurity removal process of the crude compound of formula (I) were also evaluated and compared.

Amorphous form slurry step: About 0.5 g of the compound of formula (I) was weighed into a 25 ml glass flask equipped with magnetic stirring, 5 mL of different solvents were added, and the mixture was slurried at room temperature and filtered. The filter cake was taken for purity detection by high-performance liquid chromatography. The selection of different solvents was performed by mixing a solvent having high solubility for the compound of formula (I) (e.g., methanol, ethanol, isopropanol, acetone, acetonitrile, ethyl acetate (EA), isopropyl acetate (IPAC), tetrahydrofuran (THF), toluene, dichloromethane (DCM), dimethylformamide (DMF), 2-methyltetrahydrofuran (2-MeTHF), dimethyl sulfoxide (DMSO), etc.) with a solvent having low solubility for the compound of formula (I) (e.g., water, methyl tert-butyl ether (MTBE), and n-heptane) at a volume ratio of 1:1 to screen for solvent systems capable of precipitating solids. The selected solvent systems for the amorphous form slurry and their corresponding purification effects are shown in Table 6.

Crystal form A purification step: 3.5 g of the crude compound of formula (I) was weighed into a 50 mL reaction flask equipped with magnetic stirring, 17.5 mL of ethanol was added, and the mixture was stirred at 25° C. for 15 minutes and filtered. The filter cake was rinsed with 5 mL of ethanol. The wet product was dried under vacuum to obtain the crystalline compound of formula (I), and the purity was detected by high-performance liquid chromatography.

Figure 14:
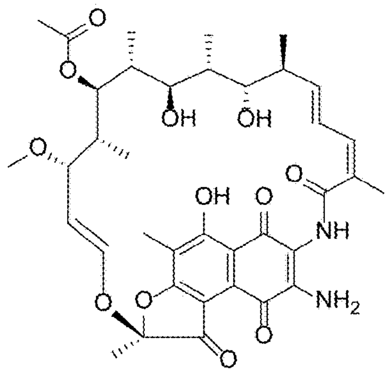
FIG. 14 shows the structural formula of the impurity RRT0.98 in the crude compound of formula (I) of the present application.

A comparison of the effects using the two purification methods is summarized in Table 6. It can be seen that, compared with the HPLC results of the crude compound of formula (I), the slurry and purification of the amorphous form sample in various mixed solvent systems basically had no impurity removal effect. In contrast, the purification effect of crystal form A was significant: it not only increased the purity of the pre-purification crude product from 92.95% to 98.2%, but also completely removed specific impurities such as RRT0.54, RRT0.92, RRT0.97, and RRT1.08. For impurities that were difficult to remove by the amorphous form slurry method, such as RRT0.63, RRT0.85, RRT0.92, RRT0.95, RRT0.97, and RRT1.21, the purification method via crystallization of the crystal form A exhibited a more significant purification effect compared with the amorphous form. The impurity removal capabilities for difficult-to-remove impurities were synchronously investigated by comparing the purification method involving column chromatography followed by slurry in ethanol/water with the crystal form A crystallization method, as shown in Table 7. The results showed that for the impurities RRT0.83 and RRT0.98, which are difficult to remove by column chromatography, the crystal form A demonstrated relatively good impurity removal effects; particularly, the impurity RRT0.98 (with structural formula shown in FIG. 14) could be controlled below the limit of detection by the crystallization method of the crystal form A. In another aspect, the column chromatography purification method is time-consuming and labor-intensive, has high production costs and high requirements for process equipment, and poses challenges in impurity control. In contrast, the crystallization purification method using the crystal form A is more environmentally friendly and offers advantages in reducing production costs and the like.

TABLE 6

Summary of purification effects of amorphous form and crystal form A

| | HPLC results (each component indicated by relative retention time RRT) | | | | | | | | | |
|---|---|---|---|---|---|---|---|---|---|---|
| Solvent | 0.54 | 0.63 | 0.85 | 0.88 | 0.92 | 0.95 | 0.97 | 1 | 1.08 | 1.21 |
| Crude product | 0.09 | 0.56 | 0.81 | 0.55 | 1.01 | 1.22 | 0.33 | 92.95 | 0.14 | 0.38 |
| IPAC + MTBE | 0.55 | 1.50 | 2.18 | N.D. | 0.80 | 1.06 | 0.62 | 79.02 | 0.46 | 2.01 |
| Toluene + MTBE | 0.20 | 0.88 | 0.95 | 1.06 | 0.68 | 1.04 | 0.40 | 91.64 | 0.20 | 0.57 |
| Ethanol + n-heptane | N.D. | 0.58 | 1.32 | N.D. | 0.77 | 1.22 | 0.41 | 90.59 | 0.16 | 0.59 |
| IPA + n-heptane | N.D. | 0.62 | 0.95 | N.D. | 0.83 | 1.20 | 0.36 | 88.82 | 0.15 | 0.43 |
| EA + n-heptane | 0.11 | 0.65 | 1.01 | N.D. | 0.89 | 1.44 | 0.43 | 91.59 | 0.14 | 0.41 |
| IPAC + n-heptane | 0.10 | 0.64 | 0.97 | N.D. | 0.99 | 1.33 | 0.40 | 91.97 | 0.16 | 0.40 |
| THF + n-heptane | N.D. | N.D. | 1.07 | N.D. | 0.65 | 1.24 | 0.43 | 91.31 | 0.17 | 0.49 |
| Toluene + n-heptane | 0.13 | 0.62 | 0.83 | 0.86 | 0.97 | 1.25 | 0.33 | 92.13 | 0.09 | 0.37 |
| DCM + n-heptane | 0.16 | 0.63 | 1.00 | 0.99 | 0.85 | 1.31 | 0.35 | 92.09 | 0.16 | 0.42 |
| 2-MeTHF + n-heptane | 0.17 | 0.66 | 1.03 | 1.12 | 0.95 | 1.09 | 0.43 | 91.61 | 0.08 | 0.31 |
| Methanol + water | 0.12 | N.D. | 0.79 | 0.62 | 0.44 | 1.74 | 0.28 | 93.15 | 0.19 | 0.37 |
| Ethanol + water | 0.07 | 0.57 | 0.82 | 0.68 | 0.36 | 1.94 | 0.28 | 93.23 | 0.11 | 0.37 |
| IPA + water | 0.12 | 0.46 | 0.83 | 0.86 | 0.37 | 1.99 | 0.31 | 92.43 | 0.09 | 0.40 |
| Acetone + water | 0.13 | 0.49 | 0.73 | 0.68 | 0.44 | 1.20 | 0.40 | 93.36 | 0.10 | N.D. |
| DMF + water | 0.07 | 0.60 | 0.77 | 0.67 | 0.91 | 1.34 | 0.32 | 92.80 | 0.10 | 0.39 |
| DMSO + water | 0.10 | 0.60 | 0.85 | 0.92 | 0.98 | 1.38 | 0.38 | 92.07 | 0.15 | 0.38 |
| Crystal form A | N.D. | 0.05 | 0.12 | 0.31 | N.D. | 0.55 | N.D. | 98.20 | N.D. | 0.06 |

TABLE 7

Summary of purification effects of amorphous form post-column chromatography slurry and crystal form A crystallization

| | | HPLC purity (%) | | |
|---|---|---|---|---|
| | | Compound of formula (I) | Impurity (RRT) | |
| Sample | | (RRT = 1) | 0.83 | 0.98 |
| Amorphous form | Crude product | 92.22 | 0.23 | 0.41 |
| | Dried product after column chromatography followed by ethanol/water slurry | 99.26 | 0.24 | 0.15 |
| Crystal form A | After purification | 98.20 | 0.11 | N.D. |

The invention claimed is:

1. A crystal form A of free base of a compound represented by formula (I), formula (I)

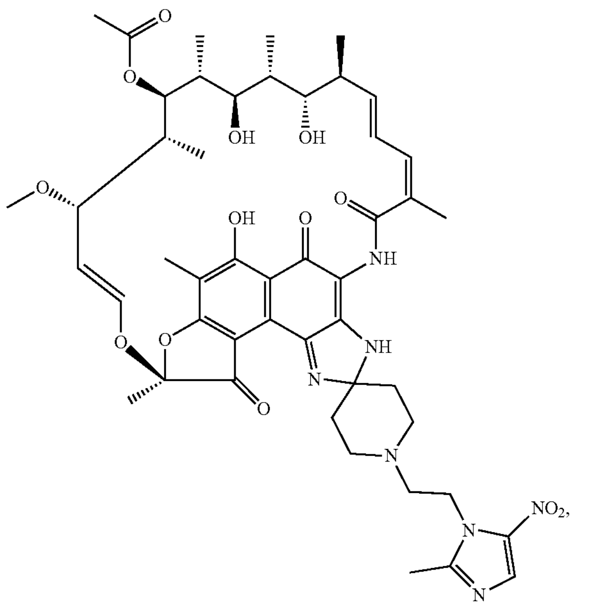

wherein the crystal form A exhibits an X-ray powder diffraction pattern having characteristic peaks at diffraction angles 2θ of 5.28°±0.2°, 7.17°±0.2°, 8.50°±0.2°, 10.66°±0.2°, 14.33°±0.2°, 15.84°±0.2°, and 18.60°±0.2°.

2. A pharmaceutical composition, comprising the crystal form A according to claim 1 and optionally a pharmaceutically acceptable carrier.

3. The pharmaceutical composition according to claim 2, further comprising a second therapeutic agent.

4. The pharmaceutical composition according to claim 3, wherein the second therapeutic agent is selected from: a proton pump inhibitor, an acid suppressant, an efflux pump inhibitor, an anesthetic, an antifungal agent, an antiviral agent, an antibacterial agent, an antiprotozoal agent, an anti-inflammatory agent, an anticoagulant, a platelet aggregation inhibitor, an antipyretic, a lipid-lowering agent, and a zinc salt.

5. A method for treating or ameliorating a disease or related disorders thereof, comprising administering to a patient in need thereof a pharmaceutical composition comprising an effective amount of the crystal form A according to claim 1.

6. The method according to claim 5, wherein the patient in need is infected with bacteria.

7. The method according to claim 6, wherein the bacteria are selected from: *Helicobacter pylori, Mycobacterium tuberculosis, Nontuberculous mycobacteria, Acinetobacter baumannii, Bacteroides fragilis, Bifidobacterium longum, Ruminococcus, Prevotella, Clostridium perfringens, Clostridium difficile, Lactobacillus acidophilus, Eggerthella lenta, Fusobacterium nucleatum, Gardnerella vaginalis, Mobiluncus mulieris, Peptostreptococcus, Porphyromonas asaccharolytica, Prevotella bivia, Propionibacterium acnes*, and *Veillonella parvula.*

8. The method according to claim 5, wherein the disease or the related disorders thereof are selected from: gastritis, gastric ulcer, bacterial vaginosis, diarrhea, pneumonia, appendicitis, cholecystitis, otitis media, endocarditis, endometritis, brain abscess, myocardial necrosis, osteomyelitis, peritonitis, empyema, salpingitis, septic arthritis, liver abscess, sinusitis, pelvic inflammatory disease, and bacteremia; and upper respiratory tract infections, lower respiratory tract infections, skin and soft tissue infections, bone and joint infections, lung infections, intra-abdominal infections, eye infections, ear infections, oral infections, and surgical infections.

9. A method for preparing the crystal form A according to claim 1, comprising crystallizing the compound represented by formula (I) in a solvent comprising methanol, ethanol or a combination thereof.

10. The method according to claim 9, wherein the crystallization in the solvent is further crystallized in methanol, ethanol or a combination thereof.

* * * * *